(12) United States Patent
Scanlan et al.

(10) Patent No.: US 6,403,373 B1
(45) Date of Patent: Jun. 11, 2002

(54) ISOLATED NUCLEIC ACID MOLECULES ASSOCIATED WITH COLON, RENAL, AND STOMACH CANCER AND METHODS OF USING THESE

(75) Inventors: Matthew J. Scanlan; Yao-Tseng Chen; Elisabeth Stockert; Lloyd J. Old, all of New York, NY (US)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/102,322

(22) Filed: Jun. 22, 1998

Related U.S. Application Data

(63) Continuation-in-part of application No. 08/948,705, filed on Oct. 10, 1997.

(51) Int. Cl.[7] .......................... C12N 5/10; C12N 15/63; C12N 15/12
(52) U.S. Cl. .................... 435/325; 435/320.1; 536/23.5
(58) Field of Search .............................. 435/325, 320.1; 536/23.5

(56) References Cited

U.S. PATENT DOCUMENTS 5,698,396 A 12/1997 Pfreundschuh ................ 435/6

OTHER PUBLICATIONS de Plaen et al., *Proc. Natl. Sci. USA* 85:2275, 1988.
Mandelboim, et al., *Nature* 369:69 1994.
van der Bruggen et al., *Science* 254:1643–1647, 1991.
Brichard et al., *J. Exp. Med.* 178:489–495, 1993.
Coulie et al., *J. Exp. Med.* 180:35–42, 1994.
Kawakami et al., *Proc. Natl. Acad. Sci. USA* 91:3515–3519, 1994.
Oettgen et al., *Immunol. Allerg. Clin. North. Am.* 10:607–637, 1990.
Sahin et al., *Proc. Natl. Acad. Sci. USA* 92:11810–11913, 1995.
Crew et al., *EMBO J* 144:2333–2340, 1995.
Sahin et al., Human neoplasms elicit multiple specific immune responses in the autologous host; Proc. Natl. Acad. Sci. USA, vol. 92, pp. 11810–11813, Dec. 1995, Immunology.*
Yasuda et al. Cloning and expression of murine high molecular mass heat shock proteins, HSP105 J. Biol. Chem. vol. 270 pp. 29718–29723, 1995.*

\* cited by examiner

*Primary Examiner*—John S. Brusca
(74) *Attorney, Agent, or Firm*—Wolf, Greenfield & Sacks, P.C.

(57) ABSTRACT

Various molecules associated with cancer are disclosed. The invention also discloses diagnostic and therapeutic methods based upon these molecules.

29 Claims, No Drawings

SEQUENCE LISTING

<160> NUMBER OF SEQ ID NOS: 22

<210> SEQ ID NO 1
<211> LENGTH: 1552
<212> TYPE: DNA
<213> ORGANISM: Homo sapiens

<400> SEQUENCE: 1

```
cttctggatg catccgagaa gctaaaactt acttatgagg aaaagtgtga aattgaggaa        60
tcccaattga agtttttgag gaacgactta gctgaatatc agagaacttg tgaagatctt       120
aaagagcaac taaagcataa agaatttctt ctggctgcta atacttgtaa ccgtgttggt       180
ggtctttgtt tgaaatgtgc tcagcatgaa gctgttcttt cccaaaccca tactaatgtt       240
catatgcaga ccatcgaaag actggttaaa gaaagagatg acttgatgtc tgcactagtt       300
tccgtaagga gcagcttggc agatacgcag caaagagaag caagtgctta tgaacaggtg       360
aaacaagttt tgcaaatatc tgaggaagcc aattttgaaa aaaccaaggc tttaatccag       420
tgtgaccagt tgaggaagga gctggagagg caggcggagc gacttgaaaa agaacttgca       480
tctcagcaag agaaaaggc cattgagaaa gacatgatga aaaaggaaat aacgaaagaa       540
agggagtaca tgggatcaaa gatgttgatc ttgtctcaga atattgccca actggaggcc       600
caggtggaaa aggttacaaa ggaaaagatt tcagctatta atcaactgga ggaaattcaa       660
agccagctgg cttctcggga aatggatgtc acaaaggtgt gtggagaaat gcgctatcag       720
ctgaataaaa ccaacatgga gaaggatgag gcagaaaagg agcacagaga gttcagagca       780
aaaactaaca gggatcttga aattaaagat caggaaatag agaaattgag aatagaactg       840
gatgaaagca acaacacctt ggaacaggag cagcagaagg cagccctggc cagagaggag       900
tgcctgagac taacagaact gctgggcgaa tctgagcacc aactgcacct caccagatct       960
gaaatagctc aactcagtca agaaaaaagg tatacatatg ataaattggg aaagttacag      1020
```

| | |
|---|---|
| agaagaaatg aagaattgga ggaacagtgt gtccagcatg ggagagtaca tgagacgatg | 1080 |
| aagcaaaggc taaggcagct ggataagcac agccaggcca cagcccagca gctggtgcag | 1140 |
| ctcctcagca agcagaacca gcttctcctg gagaggcaga gcctgtcgga agaggtggac | 1200 |
| cggctgcgga cccagttacc cagcatgcca caatctgatt gctgacctgg atggaacaga | 1260 |
| gtgaaataaa tgaattacaa agagatattt acattcatct ggtttagact taatatgcca | 1320 |
| caacgcacca cgaccttccc agggtgacac cgcctcagcc tgcagtgggg ctggtcctca | 1380 |
| tcaacgcggg cgctgtcccc gcacgcagtc gggctggagc tggagtctga ctctagctga | 1440 |
| gcagactcct ggtgtatgtt ttcagaaatg gcttgaagtt atgtgtttaa atctgctcat | 1500 |
| tcgtatgcta ggttatacat atgattttca ataaatgaac ttttttaaaga aa | 1552 |

<210> SEQ ID NO 2
<211> LENGTH: 2885
<212> TYPE: DNA
<213> ORGANISM: Homo sapiens

<400> SEQUENCE: 2

| | |
|---|---|
| ggaattcctc ttgtcgaagt caaaggagcc cacaccaggc ggcctcaacc attccctccc | 60 |
| acagcacccc aaatgctggg gagcccacca tgcttctttg gaccagagtt cccctcccca | 120 |
| gagcggcccc cctgggacgc ctccctccta caaactgcct ttgcctgggc cctacgacag | 180 |
| tcgagacgac ttcccccctcc gcaaaacagc tctgaaccc aacttgaaag tgcgttcaag | 240 |
| gctaaaacag aaggtggctg agcggagaag cagtcccctc ctgcgtcgca aggatgggac | 300 |
| tgttattagc acctttaaga agagagctgt tgagatcaca ggtgccgggc ctggggcgtc | 360 |
| gtccgtgtgt aacagcgcac ccggctccgg ccccagctct cccaacagct cccacagcac | 420 |
| catcgctgag aatggcttta ctggctcagt ccccaacatc cccactgaga tgctccctca | 480 |
| gcaccgagcc ctccctctgg acagctcccc caaccagttc agcctctaca cgtctccttc | 540 |
| tctgcccaac atctccctag ggctgcaggc cacggtcact gtcaccaact cacacctcac | 600 |
| tgcctccccg aagctgtcga cacagcagga ggccgagagg caggccctcc agtccctgcg | 660 |
| gcagggtggc acgctgaccg gcaagttcat gagcacatcc tctattcctg ctgcctgct | 720 |
| gggcgtggca ctggagggcg acgggagccc cacgggcat gcctccctgc tgcagcatgt | 780 |
| gctgttgctg gagcaggccc ggcagcagag caccctcatt gctgtgccac tccacgggca | 840 |
| gtccccacta gtgacgggtg aacgtgtggc caccagcatg cggacggtag gcaagctccc | 900 |
| gcggcatcgg cccctgagcc gcactcagtc ctcaccgctg ccgcagagtc cccaggccct | 960 |
| gcagcagctg gtcatgcaac aacagcacca gcagttcctg gagaagcaga gcagcagca | 1020 |
| gctacagctg ggcaagatcc tcaccaagac aggggagctg cccaggcagc ccaccaccca | 1080 |
| ccctgaggag acagaggagg agctgacgga gcagcaggag gtcttgctgg gggagggagc | 1140 |
| cctgaccatg ccccgggagg gctccacaga gagtgagagc acacaggaag acctggagga | 1200 |
| ggaggacgag gaagaggatg gggaggagga ggaggattgc atccaggtta aggacgagga | 1260 |
| gggcgagagt ggtgctgagg aggggcccga cttggaggag cctggtgctg gatacaaaaa | 1320 |
| actgttctca gatgcccaac cgctgcaacc tttgcaggtg taccaagcgc ccctcagcct | 1380 |
| ggccactgtg cccaccaag ccctgggccg tacccaatcc tcccctgctg ccctgggggg | 1440 |
| catgaagaac cccccagacc aaaccgtcaa gcacctcttc accacaagtg tggtctacga | 1500 |
| cacgttcatg ctaaagcacc agtgcatgtg cgggaacaca cacgtgcacc tgagcatgc | 1560 |
| tggccggatc cagagcatct ggtcccggct gcaggagaca ggcctgctta gcaagtgcga | 1620 |

```
gcggatccga ggtcgcaaag ccacgctaga tgagatccag acagtgcact ctgaatacca      1680
caccctgctc tatgggacca gtcccctcaa ccggcagaag ctagacagca agaagttgct      1740
cggtcccatc agccagaaga tgtatgctgt gctgccttgt gggggcatcg gggtggacag      1800
tgacaccgtg tggaatgaga tgcactcctc cagtgctgtg cgcatggcag tgggctgcct      1860
gctggagctg gccttcaagg tggctgcagg agagctcaag aatggatttg ccatcatccg      1920
gcccccagga caccacgccg aggaatccac agccatggga ttctgcttct tcaactctgt      1980
agccatcacc gcaaaactcc tacagcagaa gttgaacgtg ggcaaggtcc tcatcgtgga      2040
ctgggacatt caccatggca atggcaccca gcaggcgttc tacaatgacc cctctgtgct      2100
ctacatctct ctgcatcgct atgacaacgg gaacttcttt ccaggctctg gggctcctga      2160
agaggttggt ggaggaccag gcgtggggta caatgtgaac gtggcatgga caggaggtgt      2220
ggaccccccc attggagacg tggagtacct tacagccttc aggacagtgg tgatgcccat      2280
tgcccacgag ttctcacctg atgtggtcct agtctccgcc gggtttgatg ctgttgaagg      2340
acatctgtct cctctgggtg gctactctgt caccgccaga tgttttggcc acttgaccag      2400
gcagctgatg accctggcag ggggccgggt ggtgctggcc ctggagggag gccatgactt      2460
gaccgccatc tgtgatgcct ctgaagcttg tgtctcggct ctgctcagtg taaagctgca      2520
gcccttggat gaggcagtct tgcagcaaaa gcccaacatc aacgcagtgg ccacgctaga      2580
gaaagtcatc gagatccaga gcaaacactg gagctgtgtg cagaagttcg ccgctggtct      2640
gggccggtcc ctgcgagggg cccaagcagg tgagaccgaa gaagccgaaa tgtgaacgcc      2700
atggccttgc tgttggtggg ggccgaacag gcccaagctg cggcagcccg ggaacacagc      2760
cccaggccgg cagaggagcc catggagcag gagcctgccc tgtgacgccc cggcccccat      2820
ccctttgggc ttcaccattg tgattttgtt tattttttct attaaaaaca aaaagttaaa      2880
aattt                                                                 2885
```

<210> SEQ ID NO 3
<211> LENGTH: 1298
<212> TYPE: DNA
<213> ORGANISM: Homo sapiens
<220> FEATURE:
<221> NAME/KEY: unsure
<222> LOCATION: 55..55
<223> OTHER INFORMATION:
<220> FEATURE:
<221> NAME/KEY: unsure
<222> LOCATION: 141..141
<223> OTHER INFORMATION:
<220> FEATURE:
<221> NAME/KEY: unsure
<222> LOCATION: 199..199
<223> OTHER INFORMATION:
<220> FEATURE:
<221> NAME/KEY: unsure
<222> LOCATION: 342..342
<223> OTHER INFORMATION:
<220> FEATURE:
<221> NAME/KEY: unsure
<222> LOCATION: 352..352
<223> OTHER INFORMATION:
<220> FEATURE:
<221> NAME/KEY: unsure
<222> LOCATION: 722..722
<223> OTHER INFORMATION:
<220> FEATURE:
<221> NAME/KEY: unsure
<222> LOCATION: 750..750
<223> OTHER INFORMATION:
<220> FEATURE:

<221> NAME/KEY: unsure
<222> LOCATION: 1058..1058
<223> OTHER INFORMATION:
<220> FEATURE:
<221> NAME/KEY: unsure
<222> LOCATION: 1101..1101
<223> OTHER INFORMATION:
<220> FEATURE:
<221> NAME/KEY: unsure
<222> LOCATION: 1144..1144
<223> OTHER INFORMATION:

<400> SEQUENCE: 3

| | | | | | |
|---|---|---|---|---|---|
| ggctgctgaa | atgactgcga | accggcttgc | agagagcctt | ctggctttga | gccancagga | 60 |
| agaactagcg | gatttgccaa | aagactacct | cttgagtgag | agtgaagatg | aggggggacaa | 120 |
| tgatggagag | agaaagcatc | naaagcttct | ggaagcaatc | agttcccttg | atggaaagaa | 180 |
| taggcggaaa | ttggctgana | ggtctgaggc | tagtctgaag | gtgtcagagt | tcaatgtcag | 240 |
| ttctgaagga | tcaggagaaa | agctggtcct | tgcagatctg | cttgagcctg | ttaaaacttc | 300 |
| atcttctttg | gccactgtga | aaaagcaact | gagtagagtc | anatcaaaga | anacagtgga | 360 |
| gttacctctg | aacaaagaag | agattgaacg | gatccacaga | gaatagcatt | caataaaacg | 420 |
| cacaagtcct | ctccaaatgg | gaccctgtcg | tcctgaagaa | ccggcaggca | gagcagctgg | 480 |
| ttttccccct | ggagaaagag | gagccagcca | ttgctcccat | tgaacatgtg | ctcagtggct | 540 |
| ggaaggcaag | aactcccctg | gagcaggaaa | ttttcaacct | cctccataag | aacaagcagc | 600 |
| cagtgacaga | ccctttactg | acccctgtgg | aaaaggcctc | tctccgagcc | atgagcctag | 660 |
| aagaggcaaa | gatgcgacga | gcagagcttc | agagggctcg | ggctctgcag | tcctactatg | 720 |
| angccaaggc | tcgaagagag | aagaaaatcn | aaagttaaaa | gtatcacaaa | gtcgtgaaga | 780 |
| aaggaaaggc | caagaaagcc | ctaaaagagt | ttgagcagct | gcggaaggtt | aatccagctg | 840 |
| ccgcactaga | agaacgaaga | aaagaggaaa | gaaggaggag | gagaaagaag | aagaacaagg | 900 |
| agaagaagaa | agaagaaggg | agaaggagaa | gaaaagaagg | agaagaggaa | aggaagaag | 960 |
| gagaaagaaa | aggagaagga | aaaggaaaag | aaggagaaga | aagaagaact | aagaagaagg | 1020 |
| agaggaagaa | taagaaggaa | agaagaaaga | aaaagtnaa | agaagaagaa | agaaggaaga | 1080 |
| aggaaagaag | aggaagaact | nagaagaaga | agaggaggag | aagaagaaag | aagaataagg | 1140 |
| aacnagaaag | aaggagaaga | agaataagaa | agaggaagaa | gaaaagaag | aaaagaagaa | 1200 |
| ggaaagaagg | agaaaaagga | agaaaaagg | aagaagaaag | tagaaagcgg | aagaaagaaa | 1260 |
| agaaagtata | agaaggaaga | agaagaaaga | aggaaaaa | | | 1298 |

<210> SEQ ID NO 4
<211> LENGTH: 2236
<212> TYPE: DNA
<213> ORGANISM: Homo sapiens

<400> SEQUENCE: 4

| | | | | | |
|---|---|---|---|---|---|
| cctggcccgg | tcgcggtcgc | ggctctttcc | agctcctggc | agccgggcac | ccgaaggaac | 60 |
| gggtcgtgca | acgacgcagc | tggacctggc | ccagccatgg | accgaaaagt | ggcccgagaa | 120 |
| ttccggcata | aggtggattt | tctgattgaa | aatgatgcag | agaaggacta | tctctatgat | 180 |
| gtgctgcgaa | tgtaccacca | gaccatggac | gtggccgtgc | tcgtgggaga | cctgaagctg | 240 |
| gtcatcaatg | aacccagccg | tctgcctctg | tttgatgcca | ttcggccgct | gatcccactg | 300 |
| aagcaccagg | tggaatatga | tcagctgacc | cccggcgct | ccaggaagct | gaaggaggtg | 360 |
| cgtctggacc | gtctgcaccc | cgaaggcctc | ggcctgagtg | tgcgtggtgg | cctggagttt | 420 |

-continued

```
ggctgtgggc tcttcatctc ccacctcatc aaaggcggtc aggcagacag cgtcgggctc    480
caggtagggg acgagatcgt ccggatcaat ggatattcca tctcctcctg tacccatgag    540
gaggtcatca acctcattcg aaccaagaaa actgtgtcca tcaaagtgag acacatcggc    600
ctgatccccg tgaaaagctc tcctgatgag cccctcactt ggcagtatgt ggatcagttt    660
gtgtcggaat ctgggggcgt gcgaggcagc ctgggctccc tggaaatcg ggaaaacaag     720 gagaagaagg tcttcatcag cctggtaggc tcccgaggcc ttggctgcag catttccagc    780
ggccccatcc agaagcctgg catctttatc agccatgtga aacctggctc cctgtctgct    840
gaggtgggat tggagatagg ggaccagatt gtcgaagtca atggcgtcga cttctctaac    900
ctggatcaca aggaggctgt aaatgtgctg aaaatagcc gcagcctgac catctccatt     960
gtagctgcag ctggccggga gctgttcatg acagaccggg agcggctggc agaggcgcgg   1020
cagcgtgagc tgcagcggca ggagcttctc atgcagaagc ggctggcgat ggagtccaac   1080
aagatcctcc aggagcagca ggagatggag cggcaaagga gaaagaaat tgcccagaag    1140 gcagcagagg aaaatgagag ataccggaag gagatggaac agattgtaga ggaggaagag    1200
aagtttaaga gcaatggga agaagactgg ggctcaaagg aacagctact cttgcctaaa    1260
accatcactg ctgaggtaca cccagtaccc cttcgcaagc caaagtatga tcagggagtg   1320
gaacctgagc tcgagcccgc agatgacctg gatggaggca cggaggagca gggagagcag   1380
gatttccgga aatatgagga aggctttgac ccctactcta tgttcacccc agagcagatc   1440
atggggaagg atgtccggct cctacgcatc aagaaggagg atccttaga cctggccctg    1500 gaaggcggtg tggactcccc cattgggaag gtggtcgttt ctgctgtgta tgagcgggga   1560
gctgctgagc ggcatggtgg cattgtgaaa ggggacgaga tcatggcaat caacggcaag   1620
attgtgacag actacaccct ggctgaggct gacgctgccc tgcagaaggc ctggaatcag   1680 ggcgggact ggatcgacct tgtggttgcc gtctgccccc caaaggagta tgacgatgag    1740
ctgaccttct tgctgaagtc aaaaggggga accaaattc acgcgttagg aaacagtgag    1800
ctccggcccc acctcgtgaa cacaaagcct cggaccagcc ttgagagagg ccacatgaca   1860
cacaccagat ggcatccttg ggacctgaat ctatcaccca ggaatctcaa actcccttg    1920 gccctgaacc agggccagat aaggaacagc tcgggccact tttttgaagg ccaatgtgga   1980
ggaaagggag cagccagccg tttgggagaa gatctcaagg atccagactc tcattccttt    2040
cctctggccc agtgaatttg gtctctccca gctttggggg actccttcct tgaaccctaa   2100
taagacccca ctggagtctc tctctctcca tccctctcct ctgccctctg ctctaattgc   2160
tgccaggatt gtcactccaa accttactct gagctcatta ataaataaa cagatttatt    2220 ttccagctta aaaaaa                                                   2236
```

<210> SEQ ID NO 5
<211> LENGTH: 2162
<212> TYPE: DNA
<213> ORGANISM: Homo sapiens

<400> SEQUENCE: 5

```
cctggcccgg tcgcggtcgc ggctctttcc agctcctggc agccgggcac ccgaaggaac     60
gggtcgtgca acgacgcagc tggacctggc ccagccatgg accgaaaagt ggcccgagaa    120
ttccggcata aggtggattt tctgattgaa aatgatgcag agaaggacta tctctatgat    180
gtgctgcgaa tgtaccacca gaccatggac gtggccgtgc tcgtgggaga cctgaagctg    240
```

```
gtcatcaatg aacccagccg tctgcctctg tttgatgcca ttcggccgct gatcccactg    300
aagcaccagg tggaatatga tcagctgacc ccccggcgct ccaggaagct gaaggaggtg    360
cgtctggacc gtctgcaccc cgaaggcctc ggcctgagtg tgcgtggtgg cctggagttt    420
ggctgtgggc tcttcatctc ccacctcatc aaaggcggtc aggcagacag cgtcgggctc    480
caggtagggg acgagatcgt ccggatcaat ggatattcca tctcctcctg tacccatgag    540
gaggtcatca acctcattcg aaccaagaaa actgtgtcca tcaaagtgag acacatcggc    600
ctgatccccg tgaaaagctc tcctgatgag cccctcactt ggcagtatgt ggatcagttt    660
gtgtcggaat ctgggggcgt gcgaggcagc ctgggctccc ctggaaatcg ggaaaacaag    720
gagaagaagg tcttcatcag cctggtaggc tcccgaggcc ttggctgcag catttccagc    780
ggccccatcc agaagcctgg catctttatc agccatgtga acctggctc cctgtctgct    840 gaggtgggat tggagatagg ggaccagatt gtcgaagtca atggcgtcga cttctctaac    900
ctggatcaca aggaggctgt aaatgtgctg aaaaatagcc gcagcctgac catctccatt    960
gtagctgcag ctggccggga gctgttcatg acagaccggg agcggctggc agaggcgcgg   1020
cagcgtgagc tgcagcggca ggagcttctc atgcagaagc ggctggcgat ggagtccaac   1080
aagatcctcc aggagcagca ggagatggag cggcaaagga gaaaagaaat tgcccagaag   1140
gcagcagagg aaaatgagag ataccggaag gagatggaac agattgtaga ggaggaagag   1200
aagtttaaga gcaatgggaa gaagactggg ggctcaaagg aacagctact cttgcctaaa   1260
accatcactg ctgaggtaca cccagtaccc cttcgcaagc caaagtgatt tccggaaata   1320
tgaggaaggc tttgaccccct actctatgtt caccccagag cagatcatgg ggaaggatgt   1380
ccggctccta cgcatcaaga aggagggatc cttagacctg gccctggaag gcggtgtgga   1440
ctcccccatt gggaaggtgg tcgtttctgc tgtgtatgag cggggagctg ctgagcggca   1500
tggtggcatt gtgaaagggg acgagatcat ggcaatcaac ggcaagattg tgacagacta   1560
caccctggct gaggctgacg ctgccctgca gaaggcctgg aatcagggcg gggactggat   1620
cgaccttgtg gttgccgtct gccccccaaa ggagtatgac gatgagctga ccttcttgct   1680
gaagtccaaa aggggaaacc aaattcacgc gttaggaaac agtgagctcc ggccccacct   1740
cgtgaacaca aagcctcgga ccagccttga gagggccac atgacacaca ccagatggca   1800
tccttgggac ctgaatctat cacccaggaa tctcaaactc cctttggccc tgaaccaggg   1860
ccagataagg aacagctcgg gccactttt tgaaggccaa tgtggaggaa agggagcagc   1920
cagccgtttg ggagaagatc tcaaggatcc agactctcat tcctttcctc tggcccagtg   1980
aatttggtct ctcccagctt tgggggactc cttccttgaa ccctaataag accccactgg   2040
agtctctctc tctccatccc tctcctctgc cctctgctct aattgctgcc aggattgtca   2100
ctccaaacct tactctgagc tcattaataa aataaacaga tttattttcc agcttaaaaa   2160
aa                                                                   2162

<210> SEQ ID NO 6
<211> LENGTH: 1789
<212> TYPE: DNA
<213> ORGANISM: Homo sapiens

<400> SEQUENCE: 6
cttctggatg catccgagaa gctaaaactt acttatgagg aaaagtgtga aattgaggaa     60
tcccaattga agttttttgag gaacgactta gctgaatatc agagaacttg tgaagatctt    120
aaagagcaac taaagcataa agaatttctt ctggctgcta atacttgtaa ccgtgttggt    180
```

-continued

```
ggtctttgtt tgaaatgtgc tcagcatgaa gctgttcttt cccaaaccca tactaatgtt      240
catatgcaga ccatcgaaag actggttaaa gaaagagatg acttgatgtc tgcactagtt      300
tccgtaagga gcagcttggc agatacgcag caaagagaag caagtgctta tgaacaggtg      360
aaacaagttt tgcaaatatc tgaggaagcc aattttgaaa aaccaaggc tttaatccag       420 tgtgaccagt tgaggaagga gctggagagg caggcgagc gacttgaaaa agaacttgca       480
tctcagcaag agaaaagggc cattgagaaa gacatgatga aaaaggaaat aacgaaagaa      540
agggagtaca tgggatcaaa gatgttgatc ttgtctcaga atattgccca actggaggcc      600
caggtggaaa aggttacaaa ggaaaagatt tcagctatta tcaactgga ggaaattcaa       660 agccagctgc ttctcgggga atggatgtc acaaaggtgt gtggagaaat gcgctatcag       720
ctgaataaaa ccaacatgga aaggatgag gcagaaaagg agcacagaga gttcagagca      780
aaaactaaca gggatcttga aattaaagat caggaaatag agaaattgag atagaactg       840 gatgaaagca acaacactt ggaacaggag cagcagaagg cagccctggc cagagaggag       900
tgcctgagac taacagaact gctgggcgaa tctgagcacc aactgcacct caccagacag      960
gaaaaagata gcattcagca gagctttagc aaggaagcaa aggcccaagc ccttcaggcc     1020
cagcaaagag agcaggagct gacacagaag atacagcaaa tggaagccca gcatgacaaa     1080
actgaaaatg aacagtattt gttgctgacc tcccagaata cattttgac aaagttaaag      1140 gaagaatgct gtacattagc caagaaactg aacaaatct ctcaaaaaac cagatctgaa      1200
atagctcaac tcagtcaaga aaaaggtat acatatgata aattgggaaa gttacagaga      1260
agaaatgaag aattggagga acagtgtgtc cagcatggga gagtacatga gacgatgaag     1320
caaaggctaa ggcagctgga taagcacagc caggccacag cccagcagct ggtgcagctc     1380
ctcagcaagc agaaccagct tctcctggag aggcagagcc tgtcggaaga ggtggaccgg     1440
ctgcggaccc agttacccag catgccacaa tctgattgct gacctggatg aacagagtg      1500 aaataaatga attacaaaga gatatttaca ttcatctggt ttagacttaa tatgccacaa     1560
cgcaccacga ccttcccagg gtgacaccgc ctcagcctgc agtggggctg gtcctcatca    1620
acgcgggcgc tgtccccgca cgcagtcggg ctggagctgg agtctgactc tagctgagca    1680
gactcctggt gtatgttttc agaaatggct tgaagttatg tgtttaaatc tgctcattcg    1740
tatgctaggt tatacatatg attttcaata aatgaacttt ttaaagaaa                1789
```

<210> SEQ ID NO 7
<211> LENGTH: 1306
<212> TYPE: DNA
<213> ORGANISM: Homo sapiens

<400> SEQUENCE: 7

```
aaaaatagcc gcagcctgac catctccatt gtagctgcag ctggccggga gctgttcatg       60
acagaccggg agcggctggc agaggcgcgg cagcgtgagc tgcagcggca ggagcttctc      120
atgcagaagc ggctggcgat ggagtccaac aagatcctcc aggagcagca ggagatggag      180
cggcaaagga gaaagaaat tgcccagaag gcagcagagg aaaatgagag ataccggaag      240
gagatggaac agattgtaga ggaggaagag aagtttaaga agcaatggga agaagactgg      300
ggctcaaagg aacagctact cttgcctaaa accatcactg ctgaggtaca cccagtaccc      360
cttcgcaagc caaagtatga tcaggagtg gaacctgagc tcgagcccgc agatgaccctg     420 gatggaggca cggaggagca gggagagcag gatttccgga aatatgagga aggctttgac      480
```

-continued

| | |
|---|---|
| ccctactcta tgttcacccc agagcagatc atggggaagg atgtccggct cctacgcatc | 540 |
| aagaaggagg gatccttaga cctggccctg gaaggcggtg tggactcccc cattgggaag | 600 |
| gtggtcgttt ctgctgtgta tgagcggga gctgctgagc ggcatggtgg cattgtgaaa | 660 |
| ggggacgaga tcatggcaat aacggcaag attgtgacag actacaccct ggctgaggct | 720 |
| gacgctgccc tgcagaaggc ctggaatcag ggcggggact ggatcgacct tgtggttgcc | 780 |
| gtctgccccc caaggagta tgacgatgag ctgaccttct tgctgaagtc caaaggggga | 840 |
| aaccaaattc acgcgttagg aaacagtgag ctccggcccc acctcgtgaa cacaaagcct | 900 |
| cggaccagcc ttgagagagg ccacatgaca cacaccagat ggcatccttg ggacctgaat | 960 |
| ctatcaccca ggaatctcaa actcccttg gccctgaacc agggccagat aaggaacagc | 1020 |
| tcgggccact ttttgaagg ccaatgtgga ggaaagggag cagccagccg tttgggagaa | 1080 |
| gatctcaagg atccagactc tcattccttt cctctggccc agtgaatttg gtctctccca | 1140 |
| gctttggggg actccttcct tgaaccctaa taagacccca ctggagtctc tctctctcca | 1200 |
| tccctctcct ctgccctctg ctctaattgc tgccaggatt gtcactccaa accttactct | 1260 |
| gagctcatta ataaaataaa cagatttatt ttccagctta aaaaaa | 1306 |

<210> SEQ ID NO 8
<211> LENGTH: 2289
<212> TYPE: DNA
<213> ORGANISM: Homo sapiens

<400> SEQUENCE: 8

| | |
|---|---|
| cctggcccgg tcgcggtcgc ggctctttcc agctcctggc agccgggcac ccgaaggaac | 60 |
| gggtcgtgca acgacgcagc tggacctggc ccagccatgg accgaaaagt ggcccgagaa | 120 |
| ttccggcata aggtggattt tctgattgaa aatgatgcag agaaggacta tctctatgat | 180 |
| gtgctgcgaa tgtaccacca gaccatggac gtggccgtgc tcgtgggaga cctgaagctg | 240 |
| gtcatcaatg aacccagccg tctgcctctg tttgatgcca ttcggccgct gatcccactg | 300 |
| aagcaccagg tggaatatga tcagctgacc ccccggcgct ccaggaagct gaaggaggtg | 360 |
| cgtctggacc gtctgcaccc cgaaggcctc ggcctgagtg tgcgtggtgg cctggagttt | 420 |
| ggctgtgggc tcttcatctc ccacctcatc aaaggcggtc aggcagacag cgtcgggctc | 480 |
| caggtagggg acgagatcgt ccggatcaat ggatattcca tctcctcctg tacccatgag | 540 |
| gaggtcatca acctcattcg aaccaagaaa actgtgtcca tcaaagtgag acacatcggc | 600 |
| ctgatccccg tgaaaagctc tcctgatgag cccctcactt ggcagtatgt ggatcagttt | 660 |
| gtgtcggaat ctgggggcgt gcgaggcagc ctgggctccc ctggaaatcg ggaaaacaag | 720 |
| gagaagaagg tcttcatcag cctggtaggc tcccgaggcc ttggctgcag catttccagc | 780 |
| ggccccatcc agaagcctgg catctttatc agccatgtga acctggctc cctgtctgct | 840 |
| gaggtgggat tggagatagg ggaccagatt gtcgaagtca atggcgtcga cttctctaac | 900 |
| ctggatcaca aggaggctgt aaatgtgctg aaaaatagcc gcagcctgac catctccatt | 960 |
| gtagctgcag ctggccggga gctgttcatg acagaccggg agcggctggc agaggcgcgg | 1020 |
| cagcgtgagc tgcagcggca ggagcttctc atgcagaagc ggctggcgat ggagtccaac | 1080 |
| aagatcctcc aggagcagca ggagatggag cggcaaagga gaaagaaat tgcccagaag | 1140 |
| gcagcagagg aaaatgagag ataccggaag gagatggaac agattgtaga ggaggaagag | 1200 |
| aagtttaaga agcaatggga agaagactgg ggctcaaagg aacagctact cttgcctaaa | 1260 |
| accatcactg ctgaggtaca cccagtaccc cttcgcaagc caaagtatga tcagggagtg | 1320 |

-continued

```
gaacctgagc tcgagcccgc agatgacctg gatggaggca cggaggagca gggagagcag      1380
ccacaggaga tgttgaagag gatggtggtt tatcaagaca gcattcaaga caagatttcc      1440
ggaaatatga ggaaggcttt gaccoctact ctatgttcac cccagagcag atcatgggga      1500
aggatgtccg gctcctacgc atcaagaagg agggatcctt agacctggcc ctggaaggcg      1560
gtgtggactc ccccattggg aaggtggtcg tttctgctgt gtatgagcgg ggagctgctg      1620
agcggcatgg tggcattgtg aaaggggacg agatcatggc aatcaacggc aagattgtga      1680
cagactacac cctggctgag gctgacgctg ccctgcagaa ggcctggaat cagggcgggg      1740
actggatcga ccttgtggtt gccgtctgcc ccccaaagga gtatgacgat gagctgacct      1800
tcttgctgaa gtccaaaagg ggaaaccaaa ttcacgcgtt aggaaacagt gagctccggc      1860
cccacctcgt gaacacaaag cctcggacca gccttgagag aggccacatg acacacacca      1920
gatggcatcc ttgggacctg aatctatcac ccaggaatct caaactccct ttggccctga      1980
accagggcca gataaggaac agctcgggcc acttttttga aggccaatgt ggaggaaagg      2040
gagcagccag ccgtttggga gaagatctca aggatccaga ctctcattcc tttcctctgg      2100
cccagtgaat ttggtctctc ccagctttgg gggactcctt ccttgaaccc taataagacc      2160
ccactggagt ctctctctct ccatccctct cctctgccct ctgctctaat tgctgccagg      2220
attgtcactc caaaccttac tctgagctca ttaataaaat aaacagattt attttccagc      2280
ttaaaaaaa                                                              2289
```

<210> SEQ ID NO 9
<211> LENGTH: 2409
<212> TYPE: DNA
<213> ORGANISM: Homo sapiens

<400> SEQUENCE: 9

```
cctggcccgg tcgcggtcgc ggctctttcc agctcctggc agccgggcac ccgaaggaac       60
gggtcgtgca acgacgcagc tggacctggc ccagccatgg accgaaaagt ggcccgagaa      120
ttccggcata aggtggattt tctgattgaa aatgatgcag agaaggacta tctctatgat      180
gtgctgcgaa tgtaccacca gaccatggac gtggccgtgc tcgtgggaga cctgaagctg      240
gtcatcaatg aacccagccg tctgcctctg tttgatgcca ttcggccgct gatcccactg      300
aagcaccagg tggaatatga tcagctgacc cccggcgct ccaggaagct gaaggaggtg      360
cgtctggacc gtctgcaccc cgaaggcctc ggcctgagtg tgcgtggtgg cctggagttt      420
ggctgtgggc tcttcatctc ccacctcatc aaaggcggtc aggcagacag cgtcgggctc      480
caggtagggg acgagatcgt ccggatcaat ggatattcca tctcctcctg tacccatgag      540
gaggtcatca acctcattcg aaccaagaaa actgtgtcca tcaaagtgag acacatcggc      600
ctgatccccg tgaaaagctc tcctgatgag cccctcactt ggcagtatgt ggatcagttt      660
gtgtcggaat ctggggggcgt gcgaggcagc ctgggctccc ctggaaatcg ggaaaacaag      720
gagaagaagg tcttcatcag cctggtaggc tcccgaggcc ttggctgcag catttccagc      780
ggccccatcc agaagcctgg catctttatc agccatgtga acctggctc cctgtctgct      840 gaggtgggat tggagatagg ggaccagatt gtcgaagtca atggcgtcga cttctctaac      900
ctggatcaca aggaggctgt aaatgtgctg aaaaatagcc gcagcctgac catctccatt      960
gtagctgcag ctgccgggga gctgttcatg acagaccggg agcggctggc agaggcgcgg     1020
cagcgtgagc tgcagcggca ggagcttctc atgcagaagc ggctggcgat ggagtccaac     1080
```

-continued

```
aagatcctcc aggagcagca ggagatggag cggcaaagga gaaagaaat tgcccagaag    1140 gcagcagagg aaaatgagag ataccggaag gagatggaac agattgtaga ggaggaagag    1200
aagtttaaga agcaatggga agaagactgg ggctcaaagg aacagctact cttgcctaaa    1260
accatcactg ctgaggtaca cccagtaccc cttcgcaagc caaagtatga tcagggagtg    1320
gaacctgagc tcgagcccgc agatgacctg gatggaggca cggaggagca gggagagcag    1380
acattttgcc caagcccaca gcctccacga ggccctggcg tgtccaccat ctccaaacct    1440
gtcatggtcc accaggagcc caatttcatc tacaggccag ctgtgaaatc tgaagttctg    1500
ccacaggaga tgttgaagag gatggtggtt tatcaagaca gcattcaaga caagatttcc    1560
ggaaatatga ggaaggcttt gaccccctact ctatgttcac cccagagcag atcatgggga    1620
aggatgtccg gctcctacgc atcaagaagg agggatcctt agacctggcc ctggaaggcg    1680
gtgtggactc ccccattggg aagtggtcg tttctgctgt gtatgagcgg ggagctgctg    1740
agcggcatgg tggcattgtg aaagggacg agatcatggc aatcaacggc aagattgtga    1800
cagactacac cctggctgag gctgacgctg ccctgcagaa ggcctggaat cagggcgggg    1860
actggatcga ccttgtggtt gccgtctgcc ccccaaagga gtatgacgat gagctgacct    1920
tcttgctgaa gtccaaaagg ggaaaccaaa ttcacgcgtt aggaaacagt gagctccggc    1980
cccacctcgt gaacacaaag cctcggacca gccttgagag aggccacatg acacacacca    2040
gatggcatcc ttgggacctg aatctatcac ccaggaatct caaactccct ttggccctga    2100
accagggcca gataaggaac agctcgggcc acttttttga aggccaatgt ggaggaaagg    2160
gagcagccag ccgtttggga gaagatctca aggatccaga ctctcattcc tttcctctgg    2220
cccagtgaat ttggtctctc ccagctttgg gggactcctt ccttgaaccc taataagacc    2280
ccactggagt ctctctctct ccatccctct cctctgccct ctgctctaat tgctgccagg    2340
attgtcactc caaaccttac tctgagctca ttaataaaat aaacagattt attttccagc    2400
ttaaaaaaa                                                            2409
```

```
<210> SEQ ID NO 10
<211> LENGTH: 1445
<212> TYPE: DNA
<213> ORGANISM: Homo sapiens
<220> FEATURE:
<221> NAME/KEY: unsure
<222> LOCATION: 1287..1287
<223> OTHER INFORMATION:
<220> FEATURE:
<221> NAME/KEY: unsure
<222> LOCATION: 1309..1309
<223> OTHER INFORMATION:
<220> FEATURE:
<221> NAME/KEY: unsure
<222> LOCATION: 1359..1359
<223> OTHER INFORMATION:

<400> SEQUENCE: 10
```

```
ctccggcagg gagtcctagc gcagactttg cggttcatgg agagtctctg ggagacaggc      60
acctgcggac gctgcagata agttacgacg cactgaaaga tgaaaattct aagctgagaa     120
gaaagctgaa tgaggttcag agcttctctg aagctcaaac agaaatggtg aggacgcttg     180
agcggaagtt agaagcaaaa atgatcaagg aggaaagcga ctaccacgac ctggagtcgg     240
tggttcagca ggtggagcag aacctggagc tgatgaccaa cgggctgta aaggcagaaa     300 accacgtcgt gaaactaaaa caggaaatca gtttgctcca ggcgcaggtc tccaacttcc     360
agcgagagaa tgaagccctg cggtgcggcc agggtgccag cctgaccgtg gtgaagcaga     420
```

```
acgccgacgt ggccctgcag aacctccggg tggtcatgaa cagtgcacag gcttccatca    480
agcaactggt ttccggagct gagacactga atcttgttgc cgaaatcctt aaatctatag    540
acagaatttc tgaagttaaa gacgaggagg aagactcttg aggaccectg ggtgttctca    600 gcatgaagct ccgtgtatac cctgaggtca ccaccgctcg atctaaatgt gcagttgtgt    660
ccttaaatat gcagtcttca cccagagtaa agtgttgatc gcaagagtcc agtgtcgtgc    720
cctcagccag ttcttggcca ccacaatggg agcagccctg ccgagttgt  ctctgtggtt    780 tctatgcagc ccttcttggc gaaattcctg cgatcttata gattctaatg agctcttgga    840
agacattgtc ataaaagcca gtgattttaa gaaaaagagt ggttctggaa tcaatgtttt    900
ccagtcccat cccagaacat cagttgtaag ataagtacaa ttggttgtcc ttgatttcat    960
aagtagaaca aacactaaat gtgcctctga gatggccacc ccgggcaggg acctgtgcct   1020
tccgccgatg ctcagggctc cctctggctc ccgggtcact cttgtggccc cagtgggtgg   1080
tccctgcagt catggcctga gtgcgcaggg gccaccgcgt ggctgctgct gtcctcctcc   1140
ggggaccacg ggggaacaag gtcacacctt ccgtgctgtg aagctgtcca gatgtgcctc   1200
tttggctggg ggttttggtg gacgtttcaa gtggcatttt gtacaatgca ggttagaatt   1260
caggaatttc aagtatgtgc ccgggtntgt caggtcccag ttgccttnt  gacggccccc   1320 ctcagaggga cggcgatgag cactaaatgc ttttttgant attttcctat agattttttt   1380
taaaactttt ttttcctcct gttccaattg atagctttct tatttaataa attctgtagt   1440
tcacc                                                                1445

<210> SEQ ID NO 11
<211> LENGTH: 1226
<212> TYPE: DNA
<213> ORGANISM: Homo sapiens

<400> SEQUENCE: 11
ctgggccgcg aggcgcggag cttgggagcg gagcccaggc cgtgccgcgc ggcgccatga     60
agggcaagga ggagaaggag ggcggcgcac ggctgggcgc tggcggcgga agccccgaga    120
agagcccgag cgcgcaggag ctcaaggagc agggcaatcg tctgttcgtg ggccgaaagt    180
acccggaggc ggcggcctgc tacggccgcg cgatcacccg gaacccgctg gtggccgtgt    240
attacaccaa ccgggccttg tgctacctga agatgcagca gcacgagcag gccctggccg    300
actgccggcg cgccctggag ctggacggca gtctgtgaa  ggcgcacttc ttcctggggc    360
agtgccagct ggagatggag agctatgatg aggccatcgc caatctgcag cgagcttaca    420
gcctggccaa ggagcagcgg ctgaacttcg gggacgacat cccagcgct  cttcgaatcg    480 cgaagaagaa gcgctggaac agcattgagg agcggcgcat ccaccaggag agcgagctgc    540
actcctacct ctccaggctc attgccgcgg agcgtgagg  ggagctggaa gagtgccagc    600
gaaaccacga gggtgatgag gacgacagcc acgtccgggc ccagcaggcc tgcattgagg    660
ccaagcacga caagtacatg gcggacatgg acgagctttt ttctcaggtg gatgagaaga    720
ggaagaagcg agacatcccc gactacctgt gtggcaagat cagctttgag ctgatgcggg    780
agccgtgcat cacgcccagt ggcatcacct acgaccgcaa ggacatcgag gagcacctgc    840
agcgtgtggg tcattttgac ccggtgaccg ggagccccct gacccaggaa cagttcatcc    900
ccaacttggc tatgaaggag gttattgacg cattcatctc tgagaatggc tgggtggagg    960
actactgagg ttccctgccc tacctggcgt cctggtccag gggagccctg gcagaagcc   1020
```

-continued

| | | | |
|---|---|---|---|
| cccggcccct aaacatagtt tatgttttg gccacccga ccgcttccc caagttctgc | | | 1080 |
| tgttggactc tggactgttt ccctctcag catcgctttt gctgggccgt gattgtcccc | | | 1140 |
| tttgtgggct ggaaaagcag gtgagggtgg gctgggctga ggccattgcc gccactatct | | | 1200 |
| gtgtaataaa atccgtgagc acgaaa | | | 1226 |

<210> SEQ ID NO 12
<211> LENGTH: 1857
<212> TYPE: DNA
<213> ORGANISM: Homo sapiens
<220> FEATURE:
<221> NAME/KEY: unsure
<222> LOCATION: 96..96
<223> OTHER INFORMATION:

<400> SEQUENCE: 12

| | | | |
|---|---|---|---|
| gtgaggggct cctttgggca ggggtagtgt ttggtgtccc tgtcttgcgt gatattgaca | | | 60 |
| aactgaagct ttcctgcacc actggactta aggaanagtg tactcgtagg cggacagctt | | | 120 |
| tagtggccgg ccggccgctc tcatccccg taaggagcag agtcctttgt actgaccaag | | | 180 |
| atgagcaaca tctacatcca ggagcctccc acgaatggga aggttttatt gaaaactaca | | | 240 |
| gctggagata ttgacataga gttgtggtcc aaagaagctc ctaaagcttg cagaaatttt | | | 300 |
| atcccaactt tgtttggaag cttattatga caataccatt tttcatagag ttgtgcctgg | | | 360 |
| tttcatagtc caaggcggag atcctactgg cacaggagt ggtggagagt ctatctatgg | | | 420 |
| agcgccattc aaagatgaat tcattcacg gttgcgtttt aatcgagag gactggttgc | | | 480 |
| catggcaaat gctggttctc atgataatgg cacccacttt ttcttcacac tgggtcgagc | | | 540 |
| agatgaactt aacaataagc ataccatctt tggaaaggtt acaggggata cagtatataa | | | 600 |
| catgttgcga ctgtcagaag tagacattga tgatgacgaa agaccacata atccacacaa | | | 660 |
| aataaaaagc tgtgaggttt tgtttaatcc ttttgatgac atcattccaa gggaaattaa | | | 720 |
| aaggctgaaa aaagagaaac cagaggagga agtaaagaaa ttgaaaccca aggcacaaa | | | 780 |
| aaattttagt ttactttcat ttggagagga agctgaggaa gaagaagagg aagtaaatcg | | | 840 |
| agttagtcag agcatgaagg gcaaaagcaa aagtagtcat gacttgctta aggatgatcc | | | 900 |
| acatctcagt tctgttccag ttgtagaaag tgaaaaaggt gatgcaccag atttagttga | | | 960 |
| tgatggagaa gatgaaagtg cagagcatga tgaatatatt gatggtgatg aaaagaacct | | | 1020 |
| gatgagagaa agaattgcca aaaaattaaa aaaggcacaca agtgcgaatg ttaaatcagc | | | 1080 |
| tggagaagga gaagtggaga agaaatcagt cagccgcagt gaagagctca gaaaagaagc | | | 1140 |
| aagacaatta aaacgggaac tcttagcagc aaaacaaaaa aaagtagaaa atgcagcaaa | | | 1200 |
| acaagcagaa aaagaagtg aagaggaaga agcccctcca gatggtgctg ttgccgaata | | | 1260 |
| cagaagagaa aagcaaaagt atgaagcttt gaggaagcaa cagtcaaaga agggaacttc | | | 1320 |
| ccgggaagat cagacccttg cactgctgaa ccagtttaaa tctaaactca ctcaagcaat | | | 1380 |
| tgctgaaaca cctgaaaatg acattcctga aacagaagta aagatgatg aaggatggat | | | 1440 |
| gtcacatgta cttcagtttg aggataaaag cagaaaagtg aaagatgcaa gcatgcaaga | | | 1500 |
| ctcagataca tttgaaatct atgatcctcg gaatccagtg aataaaagaa ggagggaaga | | | 1560 |
| aagcaaaaag ctgatgagag agaaaaaaga aagaagataa aatgagaata atgataacca | | | 1620 |
| gaacttgctg gaaatgtgcc tacaatggcc ttgtaacagc cattgttccc aacagcatca | | | 1680 |
| cttagggggtg tgaaaagaag tatttttgaa cctgttgtct ggttttgaaa aacaattatc | | | 1740 |
| ttgttttgca aattgtggaa tgatgtaagc aaatgctttt ggttactggt acatgtgttt | | | 1800 |

```
<210> SEQ ID NO 13
<211> LENGTH: 1537
<212> TYPE: DNA
<213> ORGANISM: Homo sapiens
<220> FEATURE:
<221> NAME/KEY: unsure
<222> LOCATION: 1157..1157
<223> OTHER INFORMATION:

<400> SEQUENCE: 13
gccgcgcgcc gatcggtcgt taccgcgagg cgctggtggc cttcaggctg gacggcgcgg      60
gtcagccctg gttcgccggc ttctgggtct tgaacagcc gcgatgtcga tcttcacccc     120
caccaaccag atccgcctaa ccaatgtggc cgtggtacgg atgaagcgtg ccgggaagcg     180
cttcgaaatc gcctgctaca aaacaaggt cgtcggctgg cggagcggcg tggaaaaaga     240
cctcgatgaa gttctgcaga cccactcagt gttttgtaaat gttctaaag gtcaggttgc     300
caaaaaggaa gatctcatca gtgcgtttgg aacagatgac caaactgaaa tctgtaagca     360
gattttgact aaaggagaag ttcaagtatc agataaagaa agacacacac aactggagca     420
gatgtttagg gacattgcaa ctattgtggc agacaaatgt gtgaatcctg aaacaaagag     480
accatacacc gtgatcctta ttgagagagc catgaaggac atccactatt cggtgaaaac     540
caacaagagt acaaaacagc aggctttgga agtgataaag cagttaaaag agaaaatgaa     600
gatagaacgt gctcacatga agcttcggtt catccttcca gtcaatgaag gcaagaactg     660
aaagaaaagc tcaagccact gatcaaggtc atagaaagtg aagattatgg ccaacagtta     720
gaaatcgtat gtctgattga cccgggctgc ttccgagaaa ttgatgagct aataaaaaag     780
gaaactaaag gcaaaggttc tttggaagta ctcaatctga aagatgtaga agaaggagat     840
gagaaatttg aatgacaccc atcaatctct tcacctctaa aacactaaag tgtttccgtt     900
tccgacggca ctgtttcatg tctgtggtct gccaaatact tgcttaaact atttgacatt     960
ttctatcttt gtgttaacag tggacacagc aaggctttcc tacataagta taataatgtg    1020
ggaatgattt ggttttaatt ataaactggg gtctaaatcc taaagcaaaa ttgaaactcc    1080
aagatgcaaa gtccagagtg gcatttttgct actctgtctc atgccttgat agctttccaa    1140
aatgaaagtt acttgangca gctccttgtgg gtgaaaagtt atttgtacag tagagtaaga    1200
ttattagggg tatgtctata caacaaaagg ggggtctttt cctaaaaaag aaaacatatg    1260
atgcttcatt tctacttaat ggaacttgtg ttctgagggt cattatggta tcgtaatgta    1320
aagcttggat gatgttcctg attatttgag gaacagatat aggaaaattg tgccggaatt    1380
accttcatt gaacatgctg ccataaatta ggttattttt ggttaaaaaa taaaagtcaa    1440
ttattttaa ttttttaagt ttataatata tattaatata ggtaaaattg tatgtaatca    1500
ataaaaccaa tttatgttt attaaactta aaaaaaa                              1537

<210> SEQ ID NO 14
<211> LENGTH: 1211
<212> TYPE: DNA
<213> ORGANISM: Homo sapiens

<400> SEQUENCE: 14
accatctttg gaaaggttac agggtatac agtatataac atgttgcgac tgtcagaagt      60
agacattgat gatgacgaaa gaccacataa tccacacaaa ataaaaagct gtgaggtttt     120
```

| | |
|---|---|
| gtttaatcct tttgatgaca tcattccaag ggaaattaaa aggctgaaaa aagagaaacc | 180 |
| agaggaggaa gtaaagaaat tgaaacccaa aggcacaaaa aatttagtt tactttcatt | 240 |
| tggagaggaa gctgaggaag aagaggagga agtaaatcga gttagtcaga gcatgaaggg | 300 |
| caaaagcaaa agtagtcatg acttgcttaa ggatgatcca catctcagtt ctgttccagt | 360 |
| tgtagaaagt gaaaaaggtg atgcagcaga tttagttgat gatggagaag atgaaagtgc | 420 |
| agagcatgat gaatatattg atggtgatga aaagaacctg atgagagaaa gaattgccaa | 480 |
| aaaattaaaa aaggacacaa gtgcgaatgt taaatcagct ggagaaggag aagtggagaa | 540 |
| gaaatcagtc agccgcagtg aagagctcag aaaagaagca agacaattaa acgggaact | 600 |
| cttagcagca gaacaaaaaa aagtagaaaa tgcagcaaaa caagcagaaa aaagaagtga | 660 |
| agaggaagaa gcccctccag atggtgctgt tgccgaatac agaagagaaa agcaaaagta | 720 |
| tgaagctctg aggaagcaac agtcaaagaa gggaacttcc cgggaagatc agacccttgc | 780 |
| actgctgaac cagtttaaat ctaaactcac tcaagcaatt gctgaaacgc tgaaaatga | 840 |
| cattcctgaa acagaagtag aagatgatga aggatggatg tcacatgtac ttcagtttga | 900 |
| ggataaaagc agaaaagtga aagatgcaag catgcaagac tcagatacat ttgaaatcta | 960 |
| tgatcctcgg aatccagtga ataaaagaag gagggaagaa agcaaaaagc tgatgagaga | 1020 |
| gaaaaaagaa agaagataaa atgagaataa tgataaccag aacttgctgg aaatgtgcct | 1080 |
| acaatggcct tgtaacagcc attgttccca acagcatcac ttaggggtgt gaaaagaagt | 1140 |
| attttgaac ctgttgtctg gttttgaaaa acaattatct tgttttgcaa attgtggaat | 1200 |
| gatgtaagca a | 1211 |

<210> SEQ ID NO 15
<211> LENGTH: 604
<212> TYPE: DNA
<213> ORGANISM: Homo sapiens

<400> SEQUENCE: 15

| | |
|---|---|
| ccttcggcaa aaaattttgg tcccaacttt ttgttccatt ccaaagggc ttaccttcat | 60 |
| tcccttagc aacagggccc ccaagaagct cccgttcatt caccttacc ttggccccca | 120 |
| ggttggaccc ccaaaggctc ccttacccca aagtgggtgg ttgaataaat cttctcagtt | 180 |
| ccctggctcc caaggcccat tgaagaagat tgtacaaggc gtgcctcaag taccccgagt | 240 |
| ggaaacagaa gcacctgcct cacttcaagc cgtggctgca cccggagcag agcccgttgc | 300 |
| cgagcctggc gctgtcggag ctgtcggtgc agcatgcgga ctcactggag aacatcgacg | 360 |
| agagcgcggt ggccgagagc agagaggagc ggatgggcgg cgcgggcggc gagggcagcg | 420 |
| acgacgacac cttcacctga gcccgcaccg cttcagggac ggagacagga ccgggcgagc | 480 |
| cctggggcgg cggccgctcc tgcactttct ccctccccc acccgcacc tggtggcacc | 540 |
| gggccaggcc caggcgggtg ctgcagcctg gctggacaga gcccaataaa cggatcccac | 600 |
| agcc | 604 |

<210> SEQ ID NO 16
<211> LENGTH: 742
<212> TYPE: DNA
<213> ORGANISM: Homo sapiens

<400> SEQUENCE: 16

| | |
|---|---|
| cccaccaggg cccctcgat gcagagacag aggtcggtgc tgaccgctgc acgtcgactg | 60 |
| cctaccagga gcagaggccc caggtggagc aagttggcaa agtcgctcct ctctccccag | 120 |

```
ggctgccggc aatgggggg cctggccccg gccctgtga ggaccccgcg ggtgctgggg      180
gagcaggtgc aggggctcc gagccctgg tgactgtcac cgtgcagtgc gccttcacag      240
tggccctgag ggcaggaaga ggagccgacc tgtccagcct gcgggcactg ctgggccaag    300
ccttccttca ccaggcccag cttgggcaat tcagttacct agccccaggt gaggacgggc    360
actgggtccc catccccgag gaggagtcgc tgcagagggc ctggcaggac gcagctgcct    420
gccccagggg gctgcagctg cagtgcaggg gagccggggg tcggccggtc ctttaccagg    480
tggtggccca gcacagatac tccgcccagg ggccagagga cctgggcttc cgacaggggg    540
acacggtgga cgtcctgtgt gaagtggacc aggcatggct ggagggccac tgtgacggcc    600
gcatcggcat cttccccaag tgcttcgtgg tccccgccgg ccctcggatg tcaggagccc    660
ccggccgcct gccccgatcc cagcagggag atcagcccta atgatgctgt gtccatgatg    720
cttttaataa aaacaacccc ca                                             742

<210> SEQ ID NO 17
<211> LENGTH: 1087
<212> TYPE: DNA
<213> ORGANISM: Homo sapiens

<400> SEQUENCE: 17
aagatgatgc ctagtaaatt acagaagaac aaacagagac tgcgaaacga tcctctcaat    60
caaaataagg gtaaaccaga cttgaataca acattgccaa ttagacaaac agcatcaatt   120
ttcaaacaac cggtaaccaa agtcacaaat catcctagta ataaagtgaa atcagaccca   180
caacgaatga atgaacagcc acgtcagctt tctgggaga agaggctaca aggacttagt   240
gcatcagatg taacagaaca aattataaaa accatggaac tacccaaagg tcttcaagga   300
gttggtccag gtagcaatga tgagaccctt ttatctgctg ttgccagtgc tttgcacaca   360
agctctgcgc caatcacagg gcaagtctcc gctgctgtgg aaaagaaccc tgctgtttgg   420
cttaacacat ctcaacccct ctgcaaagct tttattgtca cagatgaaga catcaggaaa   480
caggaagagc gagtacagca agtacgcaag aaattggaag aagcactgat ggcagacatc   540
ttgtcgcgag ctgctgatac agaagagatg gatattgaaa tggacagtgg agatgaagcc   600
taagaatatg atcaggtaac tttcgaccga cttccccaa gagaaaattc ctagaaattg    660
aacaaaaatg tttccactgg cttttgcctg taagaaaaaa aatgtacccg agcacataga   720 gcttttaat agcactaacc aatgccttt tagatgtatt tttgatgtat atatctatta    780
ttcaaaaaat catgtttatt ttgagtccta ggacttaaaa ttagtctttt gtaatatcaa   840
gcaggaccct aagatgaagc tgagcttttg atgccaggtg caatttactg gaaatgtagc   900
acttacgtaa aacatttgtt tcccccacag ttttaataag aacagatcag gaattctaaa   960
taaatttccc agttaaagat tattgtgact tcactgtata taaacatatt tttatacttt  1020
attgaaaggg gacacctgta cattcttcca tcgtcactgt aaagacaaat aaatgattat  1080
attcaca                                                            1087

<210> SEQ ID NO 18
<211> LENGTH: 5878
<212> TYPE: DNA
<213> ORGANISM: Homo sapiens
<220> FEATURE:
<221> NAME/KEY: unsure
<222> LOCATION: 2237..2237
<223> OTHER INFORMATION:
<220> FEATURE:
```

```
<221> NAME/KEY: unsure
<222> LOCATION: 2260..2260
<223> OTHER INFORMATION:
<220> FEATURE:
<221> NAME/KEY: unsure
<222> LOCATION: 2305..2305
<223> OTHER INFORMATION:
<220> FEATURE:
<221> NAME/KEY: unsure
<222> LOCATION: 2315..2315
<223> OTHER INFORMATION:
<220> FEATURE:
<221> NAME/KEY: unsure
<222> LOCATION: 2355..2355
<223> OTHER INFORMATION:
<220> FEATURE:
<221> NAME/KEY: unsure
<222> LOCATION: 2420..2420
<223> OTHER INFORMATION:
<220> FEATURE:
<221> NAME/KEY: unsure
<222> LOCATION: 2421..2421
<223> OTHER INFORMATION:
<220> FEATURE:
<221> NAME/KEY: unsure
<222> LOCATION: 2423..2423
<223> OTHER INFORMATION:
<220> FEATURE:
<221> NAME/KEY: unsure
<222> LOCATION: 2490..2490
<223> OTHER INFORMATION:
<220> FEATURE:
<221> NAME/KEY: unsure
<222> LOCATION: 2523..2523
<223> OTHER INFORMATION:

<400> SEQUENCE: 18
```

| | | | | |
|---|---|---|---|---|
| aagagtaaaa | gctactcttt | cagagagaaa | aataggagat | tcatgtgaca aagatttgcc | 60 |
| tctgaaattt | tgtgagttcc | cacagaagac | tataatgcct | ggatttaaaa caactgtata | 120 |
| tgtttctcat | ataaatgacc | tttcagactt | ttatgttcaa | ctaatagaag atgaagctga | 180 |
| aattagtcat | ctttcagaga | gattaaacag | tgttaaaaca | aggcccgaat attatgtagg | 240 |
| tccacctttg | caaagaggag | atatgatatg | tgctgttttc | ccagaagata atttatggta | 300 |
| tcgtgctgtg | atcaaggagc | aacaacccaa | tgaccttctc | tctgtgcagt ttatagatta | 360 |
| tggcaatgtt | tctgtggttc | atactaacaa | aataggtagg | cttgaccttg ttaatgcaat | 420 |
| attgccgggg | ttgtgcattc | attgctcctt | gcagggattt | gaggttcctg acaataaaaa | 480 |
| ttctaagaaa | atgatgcatt | acttttccca | acggaccagc | gaggctgcaa taagatgtga | 540 |
| atttgttaaa | tttcaagaca | gatgggaagt | tattcttgct | gatgaacatg ggatcatagc | 600 |
| agatgatatg | attagcaggt | atgctctcag | tgaaaaatct | caagtagaac tttctaccca | 660 |
| agtaattaaa | agtgccagtt | caaagtctgt | taacaaatca | gacattgaca cttcagtatt | 720 |
| tcttaactgg | tataatccag | aaaaaaaaat | gataagagct | tatgccactg tgatagatgg | 780 |
| acctgagtac | ttttggtgtc | agtttgctga | tacggagaaa | cttcagtgtt tagaagtaga | 840 |
| agtacagact | gctggagaac | aggtagcaga | caggagaaat | tgtatcccat gtccttatat | 900 |
| tggagatcct | tgtatagtaa | gatacagaga | agatggacat | tattataggg cacttatcac | 960 |
| taatatttgt | gaagattatc | ttgtatctgt | caggcttgtg | gactttggaa acattgaaga | 1020 |
| ctgtgtggac | ccaaaagcac | tctgggccat | tccttctgaa | cttctgtcgg ttcccatgca | 1080 |
| agcctttcca | tgttgcctct | cagggtttaa | catttcagaa | ggattatgtt ctcaagaggg | 1140 |
| aaatgactat | ttctatgaaa | taataacaga | agatgtgttg | gaaataacaa tactagaaat | 1200 |
| cagaagggat | gtttgtgata | tcccttttagc | aattgttgac | ttgaaaagca aggtaaaag | 1260 |

```
tattaatgag aaaatggaga aatattctaa gactggtatt aaaagtgctc ttccctatga   1320
aaatattgac tcagagataa agcagactct tgggtcctac aatcttgatg taggacttaa   1380
gaaattaagt aataaagctg tacaaaataa aatatatatg aacaacaga cagatgagct    1440 tgctgaaata actgaaaaag atgtaaacat tattggaacc aaaccaagta acttccgtga   1500
ccctaaaact gataacattt gtgaagggtt tgaaaacccc tgcaaagata aaattgatac   1560
tgaggaactg gaaggtgaat tagagtgcca tctggttgac aaagcagagt ttgatgataa   1620 ataccctgatt acaggattta acacattact accacatgct aatgaaacaa aggagatact   1680
agaactgaat tcacttgagg tgccgctttc tcctgatgat gaatcaaaag aattcttaga   1740
actggaatct attgagttac agaattctct ggtggtggat gaagaaaaag gggagctaag   1800
cccggtgcca ccgaatgtgc cactctccca agagtgtgtc acaaaaggcg ccatggagct   1860
atttacactg cagcttcctc tcagctgtga agctgagaaa cagccagaac tagaactacc   1920
tacagcccag ctgcctttag atgacaagat ggatcctttg tctttaggag ttagtcagaa   1980
agcacaggaa tccatgtgta ctgaggacat gagaaagtca agttgtgtag aatcttttga   2040
tgaccagcgc aggatgtcat tgcatctaca tggagcagat tgtgatccta aaacacagaa   2100
tgaaatgaat atatgtgaag aagaatttgt agagtataaa acagggatg ccatttcggc    2160 attgatgcct ttttctctga ggaagaaagc agtgatggaa gcaagcacaa taatggttta   2220
ccagatcata tttcagntca attacagaac acctacactn tgaaagcctt tactgttgga   2280
tctaaatgtg ttgtgtggtc aagtntaaga aacanatggt ctaaatgtga gattttagaa   2340
acagctgaag aaggnacaag ggttttgaac ctttcaaatg gtatggagga gatagtgaac   2400
cctgagaatg tctggaatgn nanacccaaa ttggataaga gtccacctga gaaaagggt    2460 ttggaggtga tggagattta accgtggatn tatagctgtg gccaatcagt cagaagctgc   2520
ccntgaacaa gtggcatctt acgcagacca acagagtatt tgagaaaatc gcagaccgag   2580
acccgaggcg gaggcggacc gcgagccggc catgtcggtg gtggggttgg acgtgggctc   2640
gcagagctgc tacatcgcgg tagcccgggc cgggggcatc gagaccatcg ccaatgagtt   2700
cagcgaccgg tgcacccccgt cagtcatatc atttggatca aaaaatagaa caatcggagt   2760
tgcagccaaa aatcagcaaa tcactcatgc aaacaatacg gtgtctaact tcaaaagatt   2820
tcatggccga gcattcaatg accccttcat tcaaaaggag aaggaaaact tgagttacga   2880
tttggttcca ttgaaaaatg gtggagttgg aataaaggta atgtacatgg gtgaagaaca   2940
tctatttagt gtggagcaga taacagccat gttgttgact aagctgaagg aaactgctga   3000
aaacagcctc aagaaaccag taacagattg tgttatttca gtcccctcct tctttacaga   3060
tgctgagagg cgatctgtgt tagatgctgc acagattgtt ggcctaaact gtttaagact   3120
tatgaatgac atgacagctg ttgctttgaa ttacggaatt tataagcagg atctcccaag   3180
cctggatgag aaacctcgga tagtggtttt tgttgatatg ggacattcag ctttttcaagt   3240 gtctgcttgt gcttttaaca agggaaaatt gaaggtactg gaacagcttt tgatccttt    3300 cttaggagga aaaaacttcg atgaaaagtt agtggaacat ttttgtgcag aatttaaaac   3360
taagtacaag ttggatgcaa aatccaaaat acgagcactc ctacgtctgt atcaggaatg   3420
tgaaaaactg aaaaagctaa tgagctctaa cagcacagac cttccactga atatcgaatg   3480
ctttatgaat gataaagatg tttccggaaa gatgaacagg tcacaatttg aagaactctg   3540
tgctgaactt ctgcaaaaga tagaagtacc cctttattca ctgttggaac aaactcatct   3600
```

-continued

```
caaagtagaa gatgtgagtg cagttgagat tgttggaggc gctacacgaa ttccagctgt      3660
gaaggaaaga attgccaaat tctttggaaa agatattagc acaacactca atgcagatga      3720
agcagtagcc agaggatgtg cattacagtg tgcaatactt tccccggcat ttaaagttag      3780
agaattttcc gtcacagatg cagttccttt tccaatatct ctgatctgga accatgattc      3840
agaagatact gaaggtgttc atgaagtctt tagtcgaaac catgctgctc ctttctccaa      3900
agttctcacc tttctgagaa gggggccttt tgagctagaa gctttctatt ctgatcccca      3960
aggagttcca tatccagaag caaaaatagg ccgctttgta gttcagaatg tttctgcaca      4020
gaaagatgga gaaaaatcta gagtaaaagt caaagtgcga gtcaacaccc atggcatttt      4080
caccatctct acggcatcta tggtggagaa agtcccaact gaggagaatg aaatgtcttc      4140
tgaagctgac atggagtgtc tgaatcagag accaccagaa aacccagaca ctgataaaaa      4200
tgtccagcaa gacaacagtg aagctggaac acagccccag gtacaaactg atgctcaaca      4260
aacctcacag tctccccctt cacctgaact tacctcagaa gaaaacaaaa tcccagatgc      4320
tgacaaagca atgaaaaaa agttgacca gcctccagaa gctaaaaagc ccaaaataaa       4380
ggtggtgaat gttgagctgc ctattgaagc caacttggtc tggcagttag ggaaagacct      4440
tcttaacatg tatattgaga cagagggtaa gatgataatg caagataaat tggaaaaaga      4500
aaggaatgat gctaaaaatg cagttgagga atatgtgtat gagttcagag acaagctgtg      4560
tggaccatat gaaaaattta tatgtgagca ggatcatcaa aattttttga gactcctcac      4620
agaaactgaa gactggctgt atgaagaagg agaggaccaa gctaaacaag catatgttga      4680
caagttggaa gaattaatga aaattggcac tccagttaaa gttcggtttc aggaagctga      4740
agaacggcca aaaatgtttg aagaactagg acagaggctg cagcattatg ccaagatagc      4800
agctgacttc agaaataagg atgagaaata caaccatatt gatgagtctg aaatgaaaaa      4860
agtggagaag tctgttaatg aagtgatgga atggatgaat aatgtcatga atgctcaggc      4920
taaaaagagt cttgatcagg atccagttgt acgtgctcag gaaattaaaa caaaaatcaa      4980
ggaattgaac aacacatgtg aacccgttgt aacacaaccg aaaccaaaaa ttgaatcacc      5040
caaactggaa agaactccaa atggcccaaa tattgataaa aaggaagaag atttagaaga      5100
caaaaacaat tttggtgctg aacctccaca tcagaatggt gaatgttacc ctaatgagaa      5160
aaattctgtt aatatggact tggactagat aaccttaaat tggcctattc cttcaattaa      5220
taaaatattt ttgccatagt atgtgactct acataacata ctgaaactat ttatattttc      5280
ttttttaagg atatttagaa attttgtgta ttatatggaa aaagaaaaaa agcttaagtc      5340
tgtagtcttt atgatcctaa aagggaaaat tgccttggta actttcagat tcctgtggaa      5400
ttgtgaattc atactaagct ttctgtgcag tctccaccatt tgcatcactg aggatgaaac      5460
tgacttttgt cttttggaga aaaaaaactg tactgcttgt tcaagagggc tgtgattaaa      5520
atctttaagc atttgttcct gccaaggtag ttttcttgca ttttgctctc cattcagcat      5580
gtgtgtgggt gtggatgttt ataaacaaga ctaagtctga cttcataagg gctttctaaa      5640
accatttctg tccaagagaa aatgacttt tgctttgata ttaaaaattc aatgagtaaa      5700
acaaaagcta gtcaaatgtg ttagcagcat gcagaacaaa aactttaaac tttctctctc      5760
actatacagt atattgtcat gtgaaagtgt ggaatggaag aaatgtcgat cctgttgtaa      5820
ctgattgtga acacttttat gagctttaaa ataaagttca tcttatggtg tcatttct       5878
```

<210> SEQ ID NO 19
<211> LENGTH: 2077

<212> TYPE: DNA
<213> ORGANISM: Homo sapiens

<400> SEQUENCE: 19

```
ctgttgattt tttggagaaa tatgggagaa acagtggaat attttttatga cattttttagg      60
aaatcacctg gcttggttgg tagtcccaca ctgactttcc ttatgataat tctacagatg     120
gaggtgactc gagcagtgat gaggataaag aataacatga aactcctgtg aagtagaac      180
tcatgactca ggttgaccaa gaggatatca ctcttcagag tggcagagat gaactaaatg     240
aggagctcat tcaggaagaa agctctgaag acgaaggaga atatgaagag gttagaaaag     300
atcaggattc tgttggtgaa atgaaggatg aaggggaaga gacttaaatt atcctgatac     360
taccattgac ttgtctcacc ttcaaccccca aggtccatc cagaaattgg cttcaaagag     420
ggaatcttct aattctagtg acagtaaatc acagagccgg agacatttgt cagccaagga     480
aagaagggaa atgaaaaaga aaaacttcc aagtgactca ggagatttag aagcgttaga     540
gggaaaggat aaagaaaaag aaagtactgt acacattgaa actcatcaga acacaagcaa     600
aaatgttgcg gctgtgcagc caatgaaacg aggacaaaag agtaaaatga aaaaaatgaa     660
agaaaaatac aaagaccagg atgaagaaga ccgtgaactt atcatgaagt tgctggggtc     720
tgcaggttca aacaaagaag aaaaagggaa gaaggggaag aaaggaaaaa caaggacga     780
acctgtgaag aaacagcccc agaaacctag aggtggacag agggtctctg acaacattaa     840
gaaagaaact ccgttccttg aggttataac tcatgagtta caagactttg ctgtagatga     900
tccacatgat gacaaggaag agcaagatct ggatcaacag ggaaatgagg aaaacctatt     960
tgattctttg acaggccagc cacatcctga agatgtacta ctgtttgcca ttccaatatg    1020
tgcccccttac accaccatga caaactacaa atataaagtg aaacttactc ctggagtgca    1080
gaaaagggga aaagctgcaa aaacagcctt gaatagtttc atgcattcca agaagcaac     1140
agcaagagaa aaagacttat tccgcagcgt aaaggacaca gatttatcaa gaaacattcc    1200
tggcaaagtg aaaagtgtct gcacccaatc ttctgaacgt aaaaaggaaa tagctgaaat    1260
gaaattctaa aatatttgag aagagccaat tttatagcct tttggaagtt caaagatgaa    1320
agcaccatgt atcaggattt ccgcattata aaaatgaact aaacattgcc ttgctatatt    1380
caccaaaagg acttaattct tgttttttttc ccagtttttat atagaggaaa cactgtctat    1440
gataggattt ccaaaagtat ttgtggacag ttaaatgcta attatataca tctgtagtta    1500
ttctacattt tcttgaaatt tgggaggtta ataccaagta ttcatttcat gatgtaaaga    1560
aactgaacag tgaagtggct tgattgctta aactattgac ttggtaagtc tactgtatat    1620
aacatctaat atatatatta caggccaaat gaactaaaca ttgccttgct atattccacca   1680
aaaggactta attcttgttt ttttcccagt tttatataga ggaaacacta tgataggatt    1740
tcctaaagta tttgtggaca gttaaatgct aattatatac atctgtagtt attctacatt    1800
ttcttgaaat ttgagaggtt aataccaagt attcatttca tgatgtaaag aaactgaaca    1860
gtgaagtggc ttgattgctt aaactattga cttggtaagt ctactgtata aacatctaa    1920
tatatatata ttataggcca gctacaaggg gtttaaatat ttaggattgt gtcttgaaaa    1980
ctaagtattg gagtggattt tcttctgctt tcattgatac ttgtcagaaa aaatattag    2040
accaaaatgt aaaatataag taataattct catgaaa                             2077
```

<210> SEQ ID NO 20
<211> LENGTH: 3309
<212> TYPE: DNA

<213> ORGANISM: Homo sapiens

<400> SEQUENCE: 20

| | | | | |
|---|---|---|---|---|
| cgcagaccga | gacccgaggc | ggaggcggac | cgcgagccgg | ccatgtcggt | ggtggggttg | 60 |
| gacgtgggct | cgcagagctg | ctacatcgcg | gtagcccggg | ccgggggcat | cgagaccatc | 120 |
| gccaatgagt | tcagcgaccg | gtgcaccccg | tcagtcatat | catttggatc | aaaaaataga | 180 |
| acaatcggag | ttgcagccaa | aaatcagcaa | atcactcatg | caaacaatac | ggtgtctaac | 240 |
| ttcaaaagat | ttcatggccg | agcattcaat | gaccccttca | ttcaaaagga | gaaggaaaac | 300 |
| ttgagttacg | atttggttcc | attgaaaaat | ggtggagttg | gaataaaggt | aatgtacatg | 360 |
| ggtgaagaac | atctatttag | tgtggagcag | ataacagcca | tgttgttgac | taagctgaag | 420 |
| gaaactgctg | aaaacagcct | caagaaacca | gtaacagatt | gtgttatttc | agtcccctcc | 480 |
| ttctttacag | atgctgagag | gcgatctgtg | ttagatgctg | cacagattgt | tggcctaaac | 540 |
| tgtttaagac | ttatgaatga | catgacagct | gttgctttga | attacggaat | ttataagcag | 600 |
| gatctcccaa | gcctggatga | gaaacctcgg | atagtggttt | tgttgatat | gggacattca | 660 |
| gcttttcaag | tgtctgcttg | tgcttttaac | aagggaaaat | tgaaggtact | gggaacagct | 720 |
| tttgatcctt | tcttaggagg | aaaaaacttc | gatgaaaagt | tagtggaaca | ttttgtgca | 780 |
| gaatttaaaa | ctaagtacaa | gttggatgca | aaatccaaaa | tacgagcact | cctacgtctg | 840 |
| tatcaggaat | gtgaaaaact | gaaaaagcta | atgagctcta | acagcacaga | ccttccactg | 900 |
| aatatcgaat | gctttatgaa | tgataaagat | gttttccgga | agatgaacag | gtcacaattt | 960 |
| gaagaactct | gtgctgaact | tctgcaaaag | atagaagtac | ccctttattc | actgttggaa | 1020 |
| caaactcatc | tcaaagtaga | gatgtgagt | gcagttgaga | ttgttggagg | cgctacacga | 1080 |
| attccagctg | tgaaggaaag | aattgccaaa | ttctttggaa | agatattag | cacaacactc | 1140 |
| aatgcagatg | aagcagtagc | cagaggatgt | gcattacagt | gtgcaatact | ttccccggca | 1200 |
| tttaaagtta | gagaattttc | cgtcacagat | gcagttcctt | ttccaatatc | tctgatctgg | 1260 |
| aaccatgatt | cagaagatac | tgaaggtgtt | catgaagtct | ttagtcgaaa | ccatgctgct | 1320 |
| cctttctcca | aagttctcac | ctttctgaga | agggggcctt | tgagctaga | agcttttctat | 1380 |
| tctgatcccc | aaggagttcc | atatccagaa | gcaaaaatag | gccgctttgt | agttcagaat | 1440 |
| gtttctgcac | agaaagatgg | agaaaaatct | agagtaaaag | tcaaagtgcg | agtcaacacc | 1500 |
| catggcattt | tcaccatctc | tacggcatct | atggtggaga | aagtcccaac | tgaggagaat | 1560 |
| gaaatgtctt | ctgaagctga | catggagtgt | ctgaatcaga | gaccaccaga | aaacccagac | 1620 |
| actgataaaa | atgtccagca | agacaacagt | gaagctggaa | cacagccccca | ggtacaaact | 1680 |
| gatgctcaac | aaacctcaca | gtctcccct | tcacctgaac | ttacctcaga | gaaaacaaa | 1740 |
| atcccagatg | ctgacaaagc | aaatgaaaaa | aagttgacc | agcctccaga | agctaaaaag | 1800 |
| cccaaaataa | aggtggtgaa | tgttgagctg | cctattgaag | ccaacttggt | ctggcagtta | 1860 |
| gggaaagacc | ttcttaacat | gtatattgag | acagagggta | agatgataat | gcaagataaa | 1920 |
| ttggaaaaag | aaaggaatga | tgctaaaaat | gcagttgagg | aatatgtgta | tgagttcaga | 1980 |
| gacaagctgt | gtggaccata | tgaaaaattt | atatgtgagc | aggatcatca | aaatttttg | 2040 |
| agactcctca | cagaaactga | agactggctg | tatgaagaag | gagaggacca | agctaaacaa | 2100 |
| gcatatgttg | acaagttgga | agaattaatg | aaaattggca | ctccagttaa | agttcggttt | 2160 |
| caggaagctg | aagaacggcc | aaaaatgttt | gaagaactag | acagaggct | gcagcattat | 2220 |
| gccaagatag | cagctgactt | cagaaataag | gatgagaaat | acaaccatat | tgatgagtct | 2280 |

-continued

```
gaaatgaaaa aagtggagaa gtctgttaat gaagtgatgg aatggatgaa taatgtcatg      2340
aatgctcagg ctaaaaagag tcttgatcag gatccagttg tacgtgctca ggaaattaaa      2400
acaaaaatca aggaattgaa caacacatgt gaacccgttg taacacaacc gaaaccaaaa      2460
attgaatcac ccaaactgga aagaactcca aatggcccaa atattgataa aaaggaagaa      2520
gatttagaag acaaaaacaa ttttggtgct gaacctccac atcagaatgg tgaatgttac      2580
cctaatgaga aaaattctgt taatatggac ttggactaga taaccttaaa ttggcctatt      2640
ccttcaatta ataaaatatt tttgccatag tatgtgactc tacataacat actgaaacta      2700
tttatatttt cttttttaag gatatttaga aattttgtgt attatatgga aaaagaaaaa      2760
aagcttaagt ctgtagtctt tatgatccta aaagggaaaa ttgccttggt aactttcaga      2820
ttcctgtgga attgtgaatt catactaagc tttctgtgca gtctcaccat ttgcatcact      2880
gaggatgaaa ctgactttg tcttttggag aaaaaaaact gtactgcttg ttcaagaggg       2940
ctgtgattaa aatctttaag catttgttcc tgccaaggta gttttcttgc attttgctct      3000
ccattcagca tgtgtgtggg tgtggatgtt tataaacaag actaagtctg acttcataag      3060
ggctttctaa aaccatttct gtccaagaga aaatgacttt ttgctttgat attaaaaatt      3120
caatgagtaa aacaaaagct agtcaaatgt gttagcagca tgcagaacaa aaactttaaa      3180 cttttctctct cactatacag tatattgtca tgtgaaagtg tggaatggaa gaaatgtcga      3240
tcctgttgta actgattgtg aacactttta tgagctttaa aataaagttc atcttatggt      3300
gtcatttct                                                              3309
```

<210> SEQ ID NO 21
<211> LENGTH: 2918
<212> TYPE: DNA
<213> ORGANISM: Homo sapiens

<400> SEQUENCE: 21

```
ataactggag ctcgcgcgcc tgcaggtcga cactagtgga tccaaagaat tcggcacgag       60
gtgacgacaa cagggacaag gactccgaga agaccaagag gtggtccaag cccaggaagc      120
gctccctgat ggagatggag gggaaggagg atgcccttta aggtgctgaa gtgcatgtac      180
tgtggacact cctttgagtc cttgcaggac ctcagcgtcc acatgatcaa aaccaagcat      240
taccagaaag tgcctctgaa ggagccagtg ccagccatca ccaaactggt ccctccacc       300 aaaaagcggg cgcttcagga cctggcgccc cctgctccc ctgagccagc aggaatggcc       360
gcagaggtgg ccctgagtga gtcagccaag gatcagaaag cagcgaaccc gtacgtcacg      420
cccaataacc gctatggcta ccagaatggc gccagctaca cctggcagtt tgaggcccgc      480
aaggcgcaga tcctcaagtg catggagtgt ggcagctccc acgacacgct gcagcagctc      540
accgcccaca tgatggtcac cgggcacttc ctgaaagtga ccacctcggc ttctaagaag      600
ggcaagcagt tggtgctgga ccctgtggtg gaagagaaga tccagtccat cccactaccg      660
cccaccaccc acacgcggct gccggcctcc agcatcaaaa agcagcccga ctctcccgcg      720
gggtccacga cttctgaaga aaagaaagag ccagagaagg agaagccgcc tgtggctggc      780
gacgcggaga agatcaagga ggagagtgag gacagcttgg agaaatttga gcccagcacc      840
ctgtacccgt acctgcgtga ggaggacctg gacgacagcc ccaagggagg gctggacatt      900
ctcaagtccc tggagaatac cgtctccacg gccattagca aagctcagaa tggtgcgccc      960
tcatggggtg gctaccccag catccatgca gcctaccagc tcccgggcac cgtgaagcca     1020
```

```
ctgccggcgg ccgtgcagag cgtgcaggtg cagccgtcct atgctggcgg cgtgaagtcg      1080
ctgtcttccg ccgagcacaa cgccctcctg cactccccag ggagcctcac gcccccaccg      1140
cacaagagca acgtgtctgc catggaggag ctggtggaga aggtcacggg caaggtcaac      1200
atcaagaagg aggagagacc ccctgagaag gagaagagct ccctggccaa ggctgcgtcc      1260
cccatagcaa aagagaataa agatttcccg aaaacggagg aagtcagcgg caaaccacag      1320
aagaagggcc ctgaggccga gacttgggaa gccaaaaagg agggaccgct ggacgttcac      1380
accccaaatg gcacagagcc tctcaaagca aaggtcacca acggctgtaa caacctgggg      1440
atcatcatgg accactcacc ggagccttcc ttcatcaacc cgctgagcgc tttgcagtcc      1500
atcatgaaca cccacctggg caaggtgtcc aagcccgtga gtccctcgct ggacccgctg      1560
gcgatgctgt acaagatcag caacagcatg ctggacaagc cggtgtaccc cgccacccct      1620
gtgaagcagg ccgatgccat cgaccgctac tattatgaaa acagcgacca gcccattgac      1680
ttaaccaagt ccaagaacaa gccgctggtg tccagcgtgg ctgattcggt ggcatcacct      1740
ctgcgggaga gcgcactcat ggacatctcc gacatggtga aaaacctcac aggccgcctg      1800
acgcccaagt cctccacgcc ctccacagtt tcagagaagt ccgatgctga tggcagcagc      1860
tttgaggagg cgttggacga gctgtcaccg gtccacaaga ggaagggccg gcagtccaac      1920
tggaacccgc agcaccttct catcctgcag gcccagttcg cctcgagctt gcgggagacc      1980
acagaaggca agtacatcat gtcggacttg ggcccgcagg agagggtgca catctcgaag      2040
tttactgggc tctccatgac caccatcagc cactggctgg ccaatgtgaa gtaccagttg      2100
aggaggacag ggggaacgaa attcctaaag aacctggaca cagggcatcc tgttttcttt      2160
tgcaacgatt gtgcctctca gttcagaact gcttctacat acataagtca tttggagaca      2220
cacttgggct tcagcctgaa ggatctctcc aagctgccac tcaatcagat tcaagaacag      2280
cagaatgttt cgaaagtcct caccaacaaa actctgggcc cactggggc caccgaggaa      2340 gacttgggct ccacattcca atgtaagctc tgcaaccgga cttttgcgaa gcaagcacgc      2400
agtcaaactg caccttagta agacccacgg caagtctccc gaggaccacc tgatctatgt      2460
gactgagttg gagaaacagt agcgtccagg tatgcaagag accgcggaac attgcactaa      2520
acgtcgtcga gctgcactag gcatggcctg agcctctgaa atcagtcttt cctttgttgc      2580
tggcccgcct ctctggacct tggttttcct acacatattt tgtatattta tatgctttct      2640
gtccgatctg tgcatgttat ttttcttttt ccgtgagtca aagtctgacc tttattttca      2700
acatctgttt ttggtgttaa gctatctttt gtaggaaata gtggggcaca ctactcagag      2760
acattattta gcagtaaaga aagacacaaa taacaatgat aaaaagacat cctaaaatgg      2820
tgaagttgcc atgacaataa aggtcataga acctggtagt gtcaaattta accctttgag      2880
gactgtaatt gcatttctgt gcctttcact tgaaaaaa                              2918
```

<210> SEQ ID NO 22
<211> LENGTH: 1898
<212> TYPE: DNA
<213> ORGANISM: Homo sapiens
<220> FEATURE:
<221> NAME/KEY: unsure
<222> LOCATION: 191..191
<223> OTHER INFORMATION:
<220> FEATURE:
<221> NAME/KEY: unsure
<222> LOCATION: 273..273
<223> OTHER INFORMATION:
<220> FEATURE:
<221> NAME/KEY: unsure -continued

```
<222> LOCATION: 315..315
<223> OTHER INFORMATION:
<220> FEATURE:
<221> NAME/KEY: unsure
<222> LOCATION: 587..587
<223> OTHER INFORMATION:
<220> FEATURE:
<221> NAME/KEY: unsure
<222> LOCATION: 594..594
<223> OTHER INFORMATION:
<220> FEATURE:
<221> NAME/KEY: unsure
<222> LOCATION: 609..609
<223> OTHER INFORMATION:
<220> FEATURE:
<221> NAME/KEY: unsure
<222> LOCATION: 618..618
<223> OTHER INFORMATION:
<220> FEATURE:
<221> NAME/KEY: unsure
<222> LOCATION: 630..630
<223> OTHER INFORMATION:
<220> FEATURE:
<221> NAME/KEY: unsure
<222> LOCATION: 655..655
<223> OTHER INFORMATION:
<220> FEATURE:
<221> NAME/KEY: unsure
<222> LOCATION: 656..656
<223> OTHER INFORMATION:
<220> FEATURE:
<221> NAME/KEY: unsure
<222> LOCATION: 693..693
<223> OTHER INFORMATION:
<220> FEATURE:
<221> NAME/KEY: unsure
<222> LOCATION: 719..719
<223> OTHER INFORMATION:
<220> FEATURE:
<221> NAME/KEY: unsure
<222> LOCATION: 1220..1220
<223> OTHER INFORMATION:
<220> FEATURE:
<221> NAME/KEY: unsure
<222> LOCATION: 1294..1294
<223> OTHER INFORMATION:
<220> FEATURE:
<221> NAME/KEY: unsure
<222> LOCATION: 1366..1366
<223> OTHER INFORMATION:
<220> FEATURE:
<221> NAME/KEY: unsure
<222> LOCATION: 1375..1375
<223> OTHER INFORMATION:
<220> FEATURE:
<221> NAME/KEY: unsure
<222> LOCATION: 1381..1381
<223> OTHER INFORMATION:
<220> FEATURE:
<221> NAME/KEY: unsure
<222> LOCATION: 1391..1391
<223> OTHER INFORMATION:
<220> FEATURE:
<221> NAME/KEY: unsure
<222> LOCATION: 1468..1468
<223> OTHER INFORMATION:
<220> FEATURE:
<221> NAME/KEY: unsure
<222> LOCATION: 1471..1471
<223> OTHER INFORMATION:
<220> FEATURE:
<221> NAME/KEY: unsure
<222> LOCATION: 1487..1487
<223> OTHER INFORMATION:
<220> FEATURE:
<221> NAME/KEY: unsure
<222> LOCATION: 1497..1497
<223> OTHER INFORMATION:
<220> FEATURE:
```

-continued

```
<221> NAME/KEY: unsure
<222> LOCATION: 1520..1520
<223> OTHER INFORMATION:
<220> FEATURE:
<221> NAME/KEY: unsure
<222> LOCATION: 1543..1543
<223> OTHER INFORMATION:
<220> FEATURE:
<221> NAME/KEY: unsure
<222> LOCATION: 1551..1551
<223> OTHER INFORMATION:
<220> FEATURE:
<221> NAME/KEY: unsure
<222> LOCATION: 1557..1557
<223> OTHER INFORMATION:
<220> FEATURE:
<221> NAME/KEY: unsure
<222> LOCATION: 1560..1560
<223> OTHER INFORMATION:
<220> FEATURE:
<221> NAME/KEY: unsure
<222> LOCATION: 1590..1590
<223> OTHER INFORMATION:
<220> FEATURE:
<221> NAME/KEY: unsure
<222> LOCATION: 1612..1612
<223> OTHER INFORMATION:
<220> FEATURE:
<221> NAME/KEY: unsure
<222> LOCATION: 1632..1632
<223> OTHER INFORMATION:
<220> FEATURE:
<221> NAME/KEY: unsure
<222> LOCATION: 1634..1634
<223> OTHER INFORMATION:
<220> FEATURE:
<221> NAME/KEY: unsure
<222> LOCATION: 1638..1638
<223> OTHER INFORMATION:
<220> FEATURE:
<221> NAME/KEY: unsure
<222> LOCATION: 1705..1705
<223> OTHER INFORMATION:
<220> FEATURE:
<221> NAME/KEY: unsure
<222> LOCATION: 1716..1716
<223> OTHER INFORMATION:
<220> FEATURE:
<221> NAME/KEY: unsure
<222> LOCATION: 1721..1721
<223> OTHER INFORMATION:
<220> FEATURE:
<221> NAME/KEY: unsure
<222> LOCATION: 1738..1738
<223> OTHER INFORMATION:
<220> FEATURE:
<221> NAME/KEY: unsure
<222> LOCATION: 1755..1755
<223> OTHER INFORMATION:
<220> FEATURE:
<221> NAME/KEY: unsure
<222> LOCATION: 1765..1765
<223> OTHER INFORMATION:
<220> FEATURE:
<221> NAME/KEY: unsure
<222> LOCATION: 1778..1778
<223> OTHER INFORMATION:
<220> FEATURE:
<221> NAME/KEY: unsure
<222> LOCATION: 1780..1780
<223> OTHER INFORMATION:
<220> FEATURE:
<221> NAME/KEY: unsure
<222> LOCATION: 1781..1781
<223> OTHER INFORMATION:
<220> FEATURE:
<221> NAME/KEY: unsure
<222> LOCATION: 1807..1807
<223> OTHER INFORMATION:
```

```
<220> FEATURE:
<221> NAME/KEY: unsure
<222> LOCATION: 1811..1811
<223> OTHER INFORMATION:
<220> FEATURE:
<221> NAME/KEY: unsure
<222> LOCATION: 1818..1818
<223> OTHER INFORMATION:
<220> FEATURE:
<221> NAME/KEY: unsure
<222> LOCATION: 1821..1821
<223> OTHER INFORMATION:
<220> FEATURE:
<221> NAME/KEY: unsure
<222> LOCATION: 1823..1823
<223> OTHER INFORMATION:
<220> FEATURE:
<221> NAME/KEY: unsure
<222> LOCATION: 1824..1824
<223> OTHER INFORMATION:
<220> FEATURE:
<221> NAME/KEY: unsure
<222> LOCATION: 1829..1829
<223> OTHER INFORMATION:
<220> FEATURE:
<221> NAME/KEY: unsure
<222> LOCATION: 1839..1839
<223> OTHER INFORMATION:
<220> FEATURE:
<221> NAME/KEY: unsure
<222> LOCATION: 1871..1871
<223> OTHER INFORMATION:
<220> FEATURE:
<221> NAME/KEY: unsure
<222> LOCATION: 1884..1884
<223> OTHER INFORMATION:

<400> SEQUENCE: 22
ccgccttggg tcagcctgct ccctgcttc ctgccgcagt gggggccgtc agcctggcca      60
cctcccagct cccaagccca ccctggggc caccgtccc cccacagcca ccctcggccc     120
tggagtcgga tggggaaggg ccgcccccca gggtgggctt tgtggacagc accatcaaga    180
gcctggacga naagctgcgg actctgctct accaggagca cgtgcccacc tcctcagcct    240
cagctgggac ccctgtggag gtgggcgaca ganacttcac cctggagccc ctgagagggg    300
accagccccg ctcanaggtc tgcgggggg acctggccct gccccagtg cctaaggagg      360 cggtctcagg gcgtgtccag ctgccccagc ccttggtgga aagtcagaa ctggccccca    420 ctcgaggggc cgtgatggag cagggcacgt cctcgtcaat gacagagtcg tctcccagga    480
gtatgctagg ctatgacaga gatggaaggc aggtggcctc agactccat gtggtcccca     540 gcgtccccca ggatgtacct gcttttgtga gacctgcacg tgtggancc acanacaggg     600 atggtggana agctgganaa agctcggcan agccccgcc gagtgacatg ggcanngtgg     660
ggggccaggc tagccacccc cagacactcg gcnctcgagc tttggggtcc cctcggaanc    720
gtccagatca ccaggatgtc agctcaccag ccaagactgt gggccgtttc tcggtggtca    780
gcactcagga cgagtggacc ctggcctccc cccacagcct gagatactct gccccacccg    840
acgtctacct ggacgaggcc ccctccagcc ccgacgtgaa gctggcagtg cggcgggcgc    900
agacggcctc ctccatcgag gtcggcgtgg gcgagcccgt gtccagcgac tctggggacg    960
agggccctcg ggcgagaccc ccggtgcaga agcaggcgtc cctgccgtg agtggcagcg    1020 tggctggcga cttcgtgaag aaggccaccg cttcctgcag aggccttctc gggccggctt   1080
cgctgggccc cgagacaccc agcagggtgg gcatgaaggt cccacgatc agcgtgacct    1140 ccttccattc ccagtcgtcc tacatcagca gcgacaatga ttcggagctc gaggatgctg   1200
```

```
acataaagaa ggagctgcan agtctgcggg agaagcacct gaaggagatc tcggagctgc    1260
agagccagca gaagcaggag atcgaagctc tgtnccgccg cctgggcaag ccactgcccc    1320
ccaacgtggg cttcttccac acggcacccc ccactggccg ccgganaaaa accancaaga    1380
ncaagctgaa ngcaggcaag ctgctaaatc ccctggtgcg gcagctcaag gtcgtggcct    1440
ccaacacagg tcacttggct gactccanca naagccctcc cgctaangac ctgcccnagc    1500
cagtgtgggg ctcactgcan acaacacggg cctgaacggg aangcagtgc anaccancan    1560
ccctgctccg tccggggctc cctgtcttcn gacatctgct ccggcttacc antgatggaa    1620
gcggaacgcg tngncaangg tcctccacca acaacctggc ccaggcctga accaagcccc    1680
acccgccctg cacgtccaag cgcangtgaa caacancaac nacaagaaag gttcttcncc    1740
gacgaactgc acaanctggt ggacnaatgg acaacaanan ngtgggggc gcgcactgaa     1800 acccacnctc nacccctnaa ncnnaaccnc aacttccana cattgaggcc cgcaggtggg    1860
ctgccctggc naagcccggc tttnaccccc ctccaaca                            1898
```

ISOLATED NUCLEIC ACID MOLECULES ASSOCIATED WITH COLON, RENAL, AND STOMACH CANCER AND METHODS OF USING THESE

RELATED APPLICATION

This application is a continuation-in-part of Ser. No. 08/948,705, filed on Oct. 10, 1997, and incorporated by reference herein.

FIELD OF THE INVENTION

This invention relates to the isolation of genes associated with renal and/or colon cancer, methods of diagnosing renal and/or colon cancer using these, and the use of other known genes in diagnosis of, as well as therapeutic approaches to treating such conditions.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. U.S.A. 85: 2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by anti-tumor cytolytic T cell clones. The biochemical approach, exemplified by, e.g., Mandelboim, et al., Nature 369: 69 (1994) incorporated by reference, is based on acidic elution of peptides which have bound to MHC-class I molecules of tumor cells, followed by reversed-phase high performance liquid chromography (HPLC). Antigenic peptides are identified after they bind to empty MHC-class I molecules of mutant cell lines, defective in antigen processing, and induce specific reactions with cytolytic T-lymphocytes ("CTLs"). These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of CTLs with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. U.S.A. 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. U.S.A. 92: 11810–11913 (1995), incorporated by reference. Also, see U.S. patent application Ser. No. 08/580,980, filed on Jun. 7, 1995 and U.S. Pat. No. 5,698,396. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

The SEREX methodology has now been applied to various tumors, including colon and renal cancer samples. Several nucleic acid molecules have been newly isolated and sequenced, and are now associated with stomach cancer. Further, a pattern of expression involving these, as well as previously isolated genes has been found to be associated with renal and colon cancer. These results are the subject of this application, which is elaborated upon in the disclosure which follows.

DETAILED DESCRIPTION OF PREFERRED EMBODIMENTS

EXAMPLE 1

Tumor samples were obtained as surgical samples, and were frozen at −80° C. until ready for use.

Total RNA was then isolated from the samples, using the well known guanidium thiocyanate method of Chirgwin, et al., Biochemistry 18: 5294–5299 (1979), incorporated by reference. The thus obtained total RNA was then purified to isolate all poly $A^+$ RNA, using commercially available products designed for this purpose.

The poly $A^+$ RNA was then converted into cDNA, and ligated into λZAP, a well known expression vector.

Three cDNA libraries were constructed in this way, using colorectal carcinoma samples. A fourth library, also from colorectal carcinoma, was prepared, albeit in a different way. The reasons for this difference will be clear in the examples, infra.

The fourth library was an IgG subtraction library, prepared by using a subtraction partner, generated by PCR amplification of a cDNA clone which encoded an IgG molecule. See, e.g., Ace et al, Endocrinology 134: 1305–1309 (1994), and incorporated by reference in its entirety.

This is done to eliminate any false, positive signals resulting from interaction of cDNA clones which encode IgG, with the IgG then interacting with the anti-human IgG used in the assay, as described infra. PCR product was biotinylated, and hybridized with denatured second strand cDNA, at 68° C. for 18 hours. Biotinylated hybrid molecules were coupled to streptavidin, and then removed by phenol chloroform extraction. Any remaining cDNA was also ligated into λZAP. All libraries were amplified, prior to immunoscreening discussed infra.

EXAMPLE 2

Immunoscreening was carried out, using sera obtained from patients undergoing routine diagnostic and therapeutic procedures. The sera were stored at −70° C. prior to use. Upon thawing, the sera were diluted at 1:10 in Tris buffered saline (pH 7.5), and were then passed through Sepharose 4B columns. First, the sera were passed through columns which had $E.$ $coli$ Y1090 lysates coupled thereto, and then lysates from bacteriophage infected $E.$ $coli$ BNN97 lysates. Final serum dilutions were then prepared in 0.2% non-fat dried milk/Tris buffered saline.

The method of Sahin et al., Proc. Natl. Acad. Sci. U.S.A. 92: 11810–11813 (1995), and U.S. Pat. No. 5,698,396, both of which are incorporated by reference, was used, with some modifications. Specifically, recombinant phages at a concentration of $4 \times 10^3$ phages per 15 cm plate (pfus), were amplified for six hours, after which they were transferred to nitrocellulose membranes for 15 hours. Then, the membranes were blocked with 5% nonfat dried milk.

As an alternative to the IgG subtraction, discussed supra, membranes were prescreened in a 1:2000 dilution of peroxidase conjugated, Fc fragment specific goat anti-human IgG, for one hour, at room temperature. Color was developed using 3,3'-diaminobenzidine tetrahydrochloride, which permitted scoring of IgG encoding clones.

Membranes were then incubated in 1:100 dilutions of autologous sera, which had been pretreated with the Sepharose 4B columns, as described supra. The filters were then incubated, in a 1:3000 dilution of alkaline phosphatase conjugated Fc fragment specific, goat anti-human IgG, for one hour, at room temperature. The indicator system 4-nitroblue tetrazolium chloride/5-bromo-4-chloro-3-indolyl-phosphate was then added, and color development assessed. Any positive clones were subcloned, and retested, except the tine on the nitrocellulose membrane was reduced to three hours. A total of forty-eight positive clones were identified.

Analysis of probes for SEQ ID NOS: 1 and 2 confirmed their universal expression.

EXAMPLE 3

Example 2 described work using autologous serum. The positive clones were then rescreened, using allogeneic serum, following the same method discussed supra, in example 2, except IgG prescreening was omitted. The allogeneic sera was obtained from sixteen normal blood donors, and twenty nine patients who had been diagnosed with colorectal cancer.

The analysis with the two types of serum revealed that fourteen reacted with a subset of sera from normal and cancer patients, twenty-eight only with autologous sera, and six with both allogeneic and autologous sera. Over 60% of the allogeneic serum samples tested reacted with at least one of these positive clones. About 20% reacted with two or more.

EXAMPLE 4

In view of the results described in example 3, further experiments were carried out using serum samples from patients with other forms of cancer, i.e., renal cancer (13 samples), lung cancer (23 samples), and breast cancer (10 samples). The results are set forth in Table I which follows:

| Clone Number | Normal Sera | Colon Cancer | Renal Cancer | Lung Cancer | Breast Cancer |
| --- | --- | --- | --- | --- | --- |
| NY-Co-8 | 0/16 | 8/29 | 1/13 | 0/23 | 0/10 |
| NY-Co-9 | 0/16 | 5/29 | 1/13 | 1/23 | 0/10 |
| NY-Co-13 | 0/16 | 5/29 | 0/13 | 0/23 | 0/10 |
| NY-Co-16 | 0/16 | 3/29 | 0/13 | 0/23 | 0/10 |
| NY-Co-20 | 0/16 | 4/29 | 0/13 | 0/23 | 0/10 |
| NY-Co-38 | 0/16 | 4/29 | 3/13 | 0/23 | 1/10 |

These are referred to hereafter as SEQ ID NO: 1 (NY-CO-8), SEQ ID NO: 2 (NY-CO-9), SEQ ID NO: 3 (NY-CO-16) and SEQ ID NO: 4 (NY-CO-38),

EXAMPLE 5

Following the screening work described supra, the cDNA inserts were purified and sequenced, following standard methods.

Of the six clones which were identified as being reactive with autologous and allogeneic cancer serum, and not with normal serum, two were found to be identical to previously identified molecules. Four others were found to have little or no homology to known sequences. These are presented as SEQ ID NOS: 1–4. Of twenty seven allogeneic colon cancer serum samples tested, 67% reacted with at least one of these antigens.

EXAMPLE 6

The expression pattern of mRNA corresponding to SEQ ID NOS: 1, 2 and 4, as well as other sequences identified via the preceding examples was determined. To do this, RT-PCR was carried out on a panel of RNA samples, taken from normal tissue. The panel contained RNA of lung, testis, small intestine, colon, breast, liver and placenta tissues. The RNA was purchased from a commercial source. RNA from a colon tumor sample was also included. All samples were set up for duplicate runs, so that genomic DNA contamination could be accounted for. In the controls, no reverse transcriptase was used.

Primers were designed which were specific for the cDNA, which would amplify 5'-fragments, from 300–400 base pairs in length. The PCR reactions were undertaken at an annealing temperature of 68°C. Where appropriate, 5' and 3'-RACE reactions were undertaken, using gene specific primers, and adapter primers, together with commercially available reagents. Specifically, SEQ ID NOS: 2 and 4 were tested using RACE. The resulting products were subcloned into vector pCR 2.1, screening via PCR using internal primers, and then sequenced.

SEQ ID NOS: 1 and 2 were found to be amplified in all tissues tested. SEQ ID NO: 4 was found in colon tumor, colon metastasis, gastric cancer, renal cancer and colon cancer cell lines Colo 204 and HT29, as well as in normal colon, small intestine, brain, stomach, testis, pancreas, liver, lung, heart, fetal brain, mammary gland, bladder, adrenal gland tissues. It is was not found in normal uterine, skeletal muscle, peripheral blood lymphocytes, placental, spleen thymus, or esophagus tissue, nor in lung cancer.

The analysis also identified differential expression of a splice variant of SEQ ID NO: 4, i.e., SEQ ID NO: 5. When the two sequences were compared, it was found that SEQ ID NO: 4 encodes a putative protein of 652 amino acids, and molecular weight of 73,337 daltons. SEQ ID NO: 5, in contrast, lacks an internal 74 base pairs, corresponding to nucleotides 1307–1380 of SEQ ID NO: 4. The deletion results in formation of a stop codon at the splice function, and a putative protein of 404 amino acids, and molecular weight 45,839. The missing segment results in the putative protein lacking a PEST protein degradation sequence, thereby suggesting a longer half life for this protein.

In additional experiments, primers designed not to differentiate between SEQ ID NOS: 4 and 5 resulted in almost universal amplification (placenta being the only exception). In contrast, when primers specific for SEQ ID NO: 5 were used differences were seen in normal pancreatic, liver, lung, heart, fetal brain, mammary gland, bladder, and adrenal gland tissue, where there was no expression of SEQ ID NO: 5 found.

EXAMPLE 7

Northern blotting was also carried out for SEQ ID NOS: 1, 2, 4 and 5. To do this, the same commercially available RNA libraries discussed supra were used.

Samples (2 ug) of polyA$^+$ RNA were analyzed from these samples, using random, $^{32}$P labelled probes 300–360 nucleotides in length, obtained from PCR products. These probes were hybridized to the RNA, for 1.5 hours, at 68° C., followed by two washes at 0.1×SSC, 0.1% SDS, 68° C., for 30 minutes each time.

SEQ ID NOS: 1 and 2 were again found to be universally expressed.

EXAMPLE 8

Further screening identified additional isoforms of SEQ ID NOS: 1 and 4. These are set forth as SEQ ID NOS: 6, 7, 8 and 9. The isoform represented by SEQ ID NO: 6 is a naturally occurring splice variant of SEQ ID NO: 1, found in normal colon. SEQ ID NO: 7, which is an isoform of SEQ ID NO: 4, was found in brain tissue, primarily spinal chord and medulla. SEQ ID NO: 8, was found in normal kidney and in colon tumors, metastasized colon cancer, renal cancer, gastric cancer, and in colon cancer cell line Colo 205. It was not found in any normal tissue other than kidney.

The nucleic acid molecule whose nucleotide sequence set forth as SEQ ID NO: 9, is a further isoform of SEQ ID NO: 4. It is similar to SEQ ID NO: 8, except it contains a long nucleotide insert encoding a longer COOH terminus. It was expressed in normal bladder and kidney cells, and renal cancer cells. It was not expressed in colon cancer cells.

It is reported in example 3, supra, that fourteen clones reacted with subsets of serum from both normal and cancer patients, while twenty eight reacted with autologous sera only. These clones were sequenced, in accordance with standard, art recognized methods. Of the clones which reacted only with autologous sera, nine appear to be previously unidentified sequences. These are set forth as SEQ ID NOS: 10–18. SEQ ID NO: 10 is 1445 nucleotides long, and shows some similarity to known sequences for myosin and tropomyosin. SEQ ID NO: 11, which is 1226 nucleotides long, contains a TPR motif. The sequence set forth in SEQ ID NO: 12 is 1857 nucleotides long, and shows similarity to cyclophillins. The nucleotide sequence set forth in SEQ ID NO: 13 is 1537 nucleotides long, and shows similarity to murine gene 22A3, which has unknown function, but resembles an unconventional form of myosin, as well as an EST for heat shock inducible mRNA. As for the molecule set forth in SEQ ID NO: 14, it appears to resemble a nucleic targeting signal protein. SEQ ID NO: 15 is 604 nucleotides long, and may encode a lysosymal protein. The molecule set forth in SEQ ID NO: 16 is 742 nucleotides long, and encodes a protein with an SH3 domain and which shows some similarity to GRB2 and human neutrophil oxidase factor. The molecule set forth in SEQ ID NO: 17 is 1087 nucleotides long, and encodes a protein which contains coiled core domains. The molecule set forth in SEQ ID NO: 18 is 2569 nucleotides long, shows some similarity with Drosophila homeotic material tumor protein, and has a DY(F)GN repeat.

Additional sequences were identified which were expressed in both normal sera and cancer cells. The sequence set forth in SEQ ID NO: 19, e.g., is 2077 nucleotides long, and was expressed by both colorectal cancer and normal cells. Analysis of the sequence showed that it possesses a nuclear targeting sequence. The molecule set forth in SEQ ID NO: 20 is 3309 nucleotides long, was expressed by colorectal cancer and normal cells, and is similar to heat shock protein 110 family members. The molecule presented in SEQ ID NO: 21 was expressed in a colon to lung metastasis, as well as by normal tissue. It is 2918 nucleotides in length. Analysis shows that it contains 2 zinc finger domains. The nucleotide sequence of SEQ ID NO: 22 was also expressed in a colon to lung metastasis, is 1898 nucleotides long, and is also expressed by normal tissue. Specifically, the reactivity of the molecules was as follows:

| SEQ ID NO: | Normal sera Reactivity | Tumor Sera Reactivity |
|---|---|---|
| 19 | 2/16 | 2/16 |
| 20 | 2/16 | 3/16 |
| 21 | 2/16 | 2/16 |
| 22 | 2/8 | 1/16 |

EXAMPLE 9

A more extensive set of experiments were carried out to study the expression pattern of SEQ ID NOS: 4, 5, 8 and 9. The methodology employed was that set out in example 6, supra. The results follow.

| | SEQ ID NO.: 4 | SEQ ID NO.: 5 | SEQ ID NO.: 8 | SEQ ID NO.: 9 |
|---|---|---|---|---|
| kidney | + | Negative | Negative | Negative |
| colon | + | Negative | Negative | Negative |
| small | | Negative | Negative | Negative |
| intest. | + | Negative | Negative | Negative |

-continued

|  | SEQ ID NO.: 4 | SEQ ID NO.: 5 | SEQ ID NO.: 8 | SEQ ID NO.: 9 |
|---|---|---|---|---|
| brain | + | Negative | Negative | Negative |
| stomach | + | Negative | Negative | Negative |
| testis | + | Negative | Negative | Negative |
| pancreas | + | Negative | Negative | Negative |
| lung | + | Negative | Negative | Negative |
| liver | + | Negative | Negative | Negative |
| heart | + | Negative | Negative | Negative |
| fetal brain | | Negative | Negative | Negative |
| mammary gland | + | Negative | Negative | Negative |
| bladder | | Negative | Negative | Negative |
| adrenal gland | + | Negative | Negative | Negative |
| uterus | | Negative | Negative | Negative |
| skeletal muscle | Negative | Negative | Negative | Negative |
| PBL | Negative | Negative | Negative | Negative |
| placenta | Negative | Negative | Negative | Negative |
| spleen | Negative | Negative | Negative | Negative |
| thymus | Negative | Negative | Negative | Negative |
| esophagus | Negative | Negative | Negative | Negative |
| Tumor Tissue | | | | |
| renal cancer (4) | + (2/4) | + (2/4) | + (2/4) | + (2/4) |
| colon primary tumors (10) | + (10/10) | + (10/10) | + (10/10) | Negative |
| colon mets (4) | + (4/4) | + (4/4) | + (4/4) | Negative |
| breast cancer (6) | + (3/6) | Negative | Negative | Negative |
| lung cancer (6) | + (6/6) | Negative | Negative | Negative |
| gastric cancer (1) | + | + | + | Not tested |
| colon cancer cell lines | | | | |
| colo 205 | + | + | + | Negative |
| HT29 | + | + | Negative | Negative |
| HCT15 | Negative | Negative | Negative | Negative |

The foregoing examples demonstrate several features of the invention. These include diagnostic methods for determining presence of transformed cells, such as colon cancer cells, in a sample. The sample may contain whole cells or it may be, e.g., a body fluid sample, or an effusion, etc., where the sample may contain cells, but generally will contain shed antigen. The experiments indicate that there is a family of proteins, expression of which is associated with colon cancer. Hence, the invention involves, inter alia, detecting at least two of the proteins encoded by any of e.g., SEQ ID NOS: 1, 2, 3, 4, 5, 8 or 9 wherein, presence of these is indicative of a pathology, such as colon cancer or other type of related condition. Exemplary of the type of diagnostic assays which can be carried out are immunoassays, amplification assays (e.g., PCR), or, what will be referred to herein as a "display array". "Display array" as used herein refers to a depiction of the protein profile of a given sample. Exemplary of such displays are 2-dimensional electrophoresis, banding patterns such as SDS-gels, and so forth. Thus, one aspect of the invention involves diagnosing colon cancer or a related condition by determining protein display of a sample, wherein a determination of at least one of the proteins, or expression of their genes, is indicative of colon cancer or a related condition. There are many ways to carry out these assays. For example, as indicated herein, antibodies to the proteins were found in patient samples. One can assay for these antibodies using, e.g., the methodology described herein, or by using a purified protein or proteins or antigenic fragment thereof, and so forth. One can also assay for the protein itself, using antibodies, which may be isolated from samples, or generated using the protein and standard techniques. This antibodies can then be labelled, if desired, and used in standard immunoassays. These antibodies or oligonucleotide probes/primers may also be used to examine biopsied tissue samples, e.g., to diagnose precancerous conditions, early stage cancers, and so forth.

Similarly, any and all nucleic acid hybridization systems can be used, including amplification assays, such as PCR, basic probe hybridization assays, and so forth. The antibodies, such as polyclonal antibodies, monoclonal antibodies, the hybridomas which produce them, recombinantly produced antibodies, binding fragments of these, hybridization kits, DNA probes, and so forth, are all additional features of the invention.

Any of these assays can also be used in progression/regression studies. One can monitor the course of an abnormality such as colon cancer which involve expression of any one of the proteins, the expression of which is governed by the nucleic acid molecules SEQ ID NOS: 1–5, simply by monitoring levels of the protein, its expression, and so forth using any or all of the methods set forth supra.

As has been indicated supra, the isolated nucleic acid molecules which comprise the nucleotide sequences set forth in SEQ ID NOS: 1–18 are new, in that they have never been isolated before. These nucleic acid molecules may be used as a source to generate colon cancer specific proteins and peptides derived therefrom, and oligonucleotide probes which can themselves be used to detect expression of these genes. Hence, a further aspect of the invention is an isolated nucleic acid molecule which comprises any of the nucleotide sequences set forth in SEQ ID NOS: 1–18, or molecules whose complements hybridize to one or more of these nucleotide sequences, under stringent conditions, expression vectors comprising these molecules, operatively linked to promoters, cell lines and strains transformed or transfected with these, and so forth. "Stringent conditions", is used herein, refers to condition such as those specified in U.S. Pat. No. 5,342,774, i.e., 18 hours of hybridization at 65° C., followed by four one hour washes at 2×SSC, 0.1% SDS, and a final wash at 0.2×SSC, more preferably 0.1×SSC, 0.1% SDS for 30 minutes, as well as alternate conditions which afford the same level of stringency, and more stringent conditions.

Especially preferred are those associated specifically with cancer, such as SEQ ID NOS: 1, 2, 3, 4, 5, 8 and 9. It should be clear that these methodologies may also be used to track the efficacy of a therapeutic regime. Essentially, one can take a baseline value for the protein or proteins being tested, using any of the assays discussed supra, administer a given therapeutic, and then monitor levels of the protein or proteins thereafter, observing changes in protein levels as indicia of the efficacy of the regime.

The identification of the proteins and nucleic acid molecules set forth herein as being implicated in pathological conditions such as colon cancer also suggests a number of therapeutic approaches to such conditions. The experiments set forth supra establish that antibodies are produced in response to expression of these proteins, suggesting their use as a vaccine. Hence, a further embodiment of the invention is the treatment of conditions which are characterized by expression of one or more of the subject proteins, via immunotherapeutic approaches. One of these approaches is the administration of an amount of one or more these proteins, or an immunogenic peptide derived therefrom in an amount sufficient to provoke or augment an immune response. The proteins or peptides may be combined with one or more of the known immune adjuvants, such as saponins GM-CSF interleukins, and so forth. If the peptides are too small to generate a sufficient antibody response, they can be coupled to the well known conjugates used to stimulate responses.

Similarly, the immunotherapeutic approaches include administering an amount of inhibiting antibodies sufficient to inhibit the protein or proteins. These antibodies may be, e.g., antibodies produced via any of the standard approaches elaborated upon supra.

T cell responses may also be elicited by using peptides derived from the proteins which then complex, non-covalently, with MHC molecules, thereby stimulating proliferation of cytolytic T cells against any such complexes in the subject. It is to be noted that the T cells may also be elicited in vitro, and then reperfused into the subject being treated.

Note that the generation of T cells and/or antibodies can also be accomplished by administering cells, preferably treated to be rendered non-proliferative, which present relevant T cell or B cell epitopes for response.

The therapeutic approaches may also include gene therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the well known BCG vaccine, and so forth.

An additional DNA based therapeutic approach is the use of a vector which comprises one or more nucleotide sequences, preferably a plurality of these, each of which encodes an immunoreactive peptide derived from the expressed proteins. One can combine these peptides expressing sequences in all possible variations, such as one from each protein, several from one or more protein and one from each of the additional proteins, a plurality from some and none from others, and so forth.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule selected from the group consisting of:
   (a) nucleic acid molecules which comprise a nucleotide sequence, the complementary sequence of which hybridizes, under stringent conditions, to at least one second nucleic acid molecule comprising a nucleotide sequence selected from the group consisting of the nucleotide sequences set forth as SEQ ID NOs: 8–18, and which encode a tumor associated antigen,
   (b) nucleic acid molecules that differ from the nucleic acid molecules of (a) in codon sequence due to the degeneracy of the genetic code, and
   (c) complements of (a) or (b).

2. An expression vector comprising the isolated nucleic acid molecule of claim 1, operably linked to a promoter.

3. A cell line or cell strain comprising the isolated nucleic acid molecule of claim 1.

4. A cell line or cell strain comprising the expression vector of claim 2.

5. The isolated nucleic acid molecule of claim 1, which comprises a nucleotide sequence selected from the group consisting of the nucleotide sequences set forth as SEQ ID NOs: 8–18.

6. The isolated nucleic acid molecule of claim 1, wherein the nucleotide sequence of the second nucleic acid molecule is SEQ ID NO:8.

7. The isolated nucleic acid molecule of claim 1, wherein the nucleotide sequence of the second nucleic acid molecule is SEQ ID NO:9.

8. The isolated nucleic acid molecule of claim 1, wherein the nucleotide sequence of the second nucleic acid molecule is SEQ ID NO:10.

9. The isolated nucleic acid molecule of claim 1, wherein the nucleotide sequence of the second nucleic acid molecule is SEQ ID NO:11.

10. The isolated nucleic acid molecule of claim 1, wherein the nucleotide sequence of the second nucleic acid molecule is SEQ ID NO:12.

11. The isolated nucleic acid molecule of claim 1, wherein the nucleotide sequence of the second nucleic acid molecule is SEQ ID NO:13.

12. The isolated nucleic acid molecule of claim 1, wherein the nucleotide sequence of the second nucleic acid molecule is SEQ ID NO:14.

13. The isolated nucleic acid molecule of claim 1, wherein the nucleotide sequence of the second nucleic acid molecule is SEQ ID NO:15.

14. The isolated nucleic acid molecule of claim 1, wherein the nucleotide sequence of the second nucleic acid molecule is SEQ ID NO:16.

15. The isolated nucleic acid molecule of claim 1, wherein the nucleotide sequence of the second nucleic acid molecule is SEQ ID NO:17.

16. The isolated nucleic acid molecule of claim 1, wherein the nucleotide sequence of the second nucleic acid molecule is SEQ ID NO:18.

17. The isolated nucleic acid molecule of claim 5, wherein the nucleotide sequence comprises SEQ ID NO:8.

18. The isolated nucleic acid molecule of claim 5, wherein the nucleotide sequence comprises SEQ ID NO:9.

19. The isolated nucleic acid molecule of claim 5, wherein the nucleotide sequence comprises SEQ ID NO:10.

20. The isolated nucleic acid molecule of claim 5, wherein the nucleotide sequence comprises SEQ ID NO:11.

21. The isolated nucleic acid molecule of claim 5, wherein the nucleotide sequence comprises SEQ ID NO:12.

22. The isolated nucleic acid molecule of claim 5, wherein the nucleotide sequence comprises SEQ ID NO:13.

23. The isolated nucleic acid molecule of claim 5, wherein the nucleotide sequence comprises SEQ ID NO:14.

24. The isolated nucleic acid molecule of claim 5, wherein the nucleotide sequence comprises SEQ ID NO:15.

25. The isolated nucleic acid molecule of claim 5, wherein the nucleotide sequence comprises SEQ ID NO:16.

26. The isolated nucleic acid molecule of claim 5, wherein the nucleotide sequence comprises SEQ ID NO:17.

27. The isolated nucleic acid molecule of claim 5, wherein the nucleotide sequence comprises SEQ ID NO:18.

28. An isolated nucleic acid molecule comprising at least two non-identical nucleotide sequences which encode non-identical peptides, wherein the non-identical nucleotide sequences are selected from the group consisting of nucleotide sequences set forth as SEQ ID NOs: 8–22.

29. The isolated nucleic acid molecule of claim 28, further comprising a nucleotide sequence selected from the group consisting of nucleotide sequences set forth as SEQ ID NOs:1–7, or fragments thereof, wherein the nucleotide sequence encodes a peptide.

* * * * *